(12) United States Patent
Imran

(10) Patent No.: US 11,730,923 B2
(45) Date of Patent: Aug. 22, 2023

(54) IMPLANTABLE DRUG DELIVERY SYSTEMS, ASSEMBLIES, AND METHODS

(71) Applicant: InCube Labs, LLC, San Jose, CA (US)

(72) Inventor: Mir A. Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 0 days.

(21) Appl. No.: 17/842,386

(22) Filed: Jun. 16, 2022

(65) Prior Publication Data

US 2023/0011575 A1 Jan. 12, 2023

Related U.S. Application Data

(60) Provisional application No. 63/219,744, filed on Jul. 8, 2021.

(51) Int. Cl.
*A61M 25/00* (2006.01)
*A61M 39/10* (2006.01)

(52) U.S. Cl.
CPC ...... *A61M 25/0075* (2013.01); *A61M 25/007* (2013.01); *A61M 39/10* (2013.01);
(Continued)

(58) Field of Classification Search
CPC .... A61M 2025/0042; A61M 2209/088; A61M 39/10; A61M 2202/0007;
(Continued)

(56) References Cited

U.S. PATENT DOCUMENTS 4,227,533 A 10/1980 Godfrey
5,693,025 A 12/1997 Stevens
(Continued)

FOREIGN PATENT DOCUMENTS

WO 0076564 A1 12/2000
WO WO-2013016351 A1 * 1/2013 ........ A61M 25/0009
WO 2021016579 A1 1/2021

OTHER PUBLICATIONS

"International Search Report and Written Opinion received in International Application No. PCT/US2022/031631 dated Oct. 7, 2022".

*Primary Examiner* — Brandy S Lee
(74) *Attorney, Agent, or Firm* — ALG Intellectual Property, LLC

(57) ABSTRACT

An illustrative drug delivery system implantable in a recipient may include a connection assembly, a source catheter, and a microcatheter. A proximal end portion of the source catheter may be configured to be fluidically connected to a fluid source configured to provide a fluid (e.g., a neurotherapeutic drug). A distal end portion of the source catheter may be configured to be fluidically connected to the connection assembly. The microcatheter may include a proximal end portion configured to be fluidically connected to the connection assembly and a distal end portion comprising an elution opening configured to elute the fluid to a target location (e.g., a brain) within a recipient. The fluid source may be configured to provide the fluid to the target location by way of the source catheter, the connection assembly, and the microcatheter.

25 Claims, 17 Drawing Sheets

(52) U.S. Cl.
CPC ............... *A61M 2025/0042* (2013.01); *A61M 2202/0007* (2013.01)

(58) Field of Classification Search
CPC ........ A61M 2025/0079; A61M 25/007; A61M 25/0075; A61M 5/14276
See application file for complete search history.

(56) References Cited

U.S. PATENT DOCUMENTS

| | | | |
|---|---|---|---|
| 6,562,023 B1 * | 5/2003 | Marrs | ............... A61M 39/0208 604/536 |
| 2002/0156430 A1 | 10/2002 | Haarala et al. | |
| 2005/0107753 A1 * | 5/2005 | Rezai | ............... A61M 5/14276 604/288.04 |
| 2010/0318061 A1 | 12/2010 | Derrick et al. | |
| 2015/0011938 A1 | 1/2015 | Gill et al. | |
| 2015/0238685 A1 | 8/2015 | Elias et al. | |
| 2015/0290445 A1 | 10/2015 | Powers et al. | |
| 2016/0015885 A1 | 1/2016 | Pananen et al. | |
| 2018/0207399 A1 * | 7/2018 | Chou | .................... A61M 25/01 |
| 2018/0228970 A1 | 8/2018 | Wostyn | |
| 2020/0305882 A1 | 10/2020 | Kristoffersen et al. | |
| 2020/0345979 A1 | 11/2020 | Loh et al. | |
| 2021/0059744 A1 | 3/2021 | Abbas et al. | |

* cited by examiner

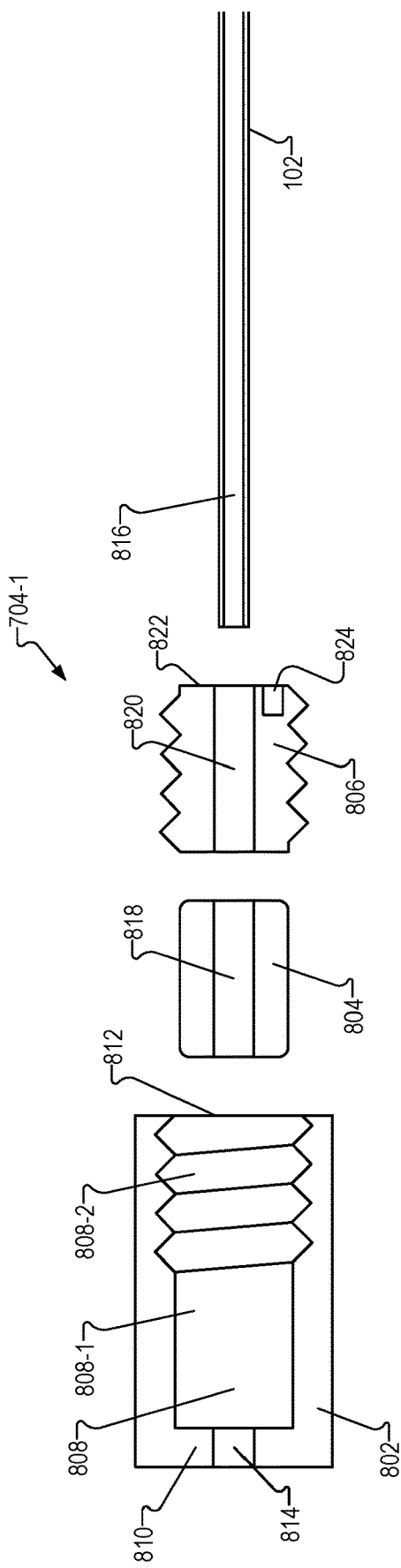
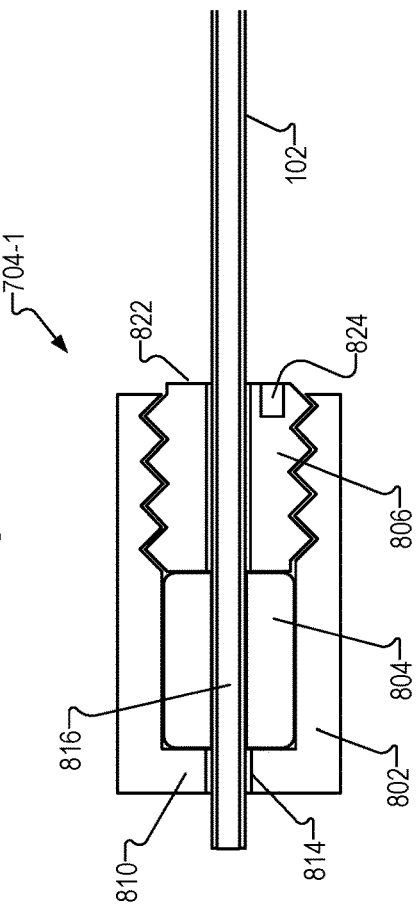
Fig. 8A
Fig. 8B

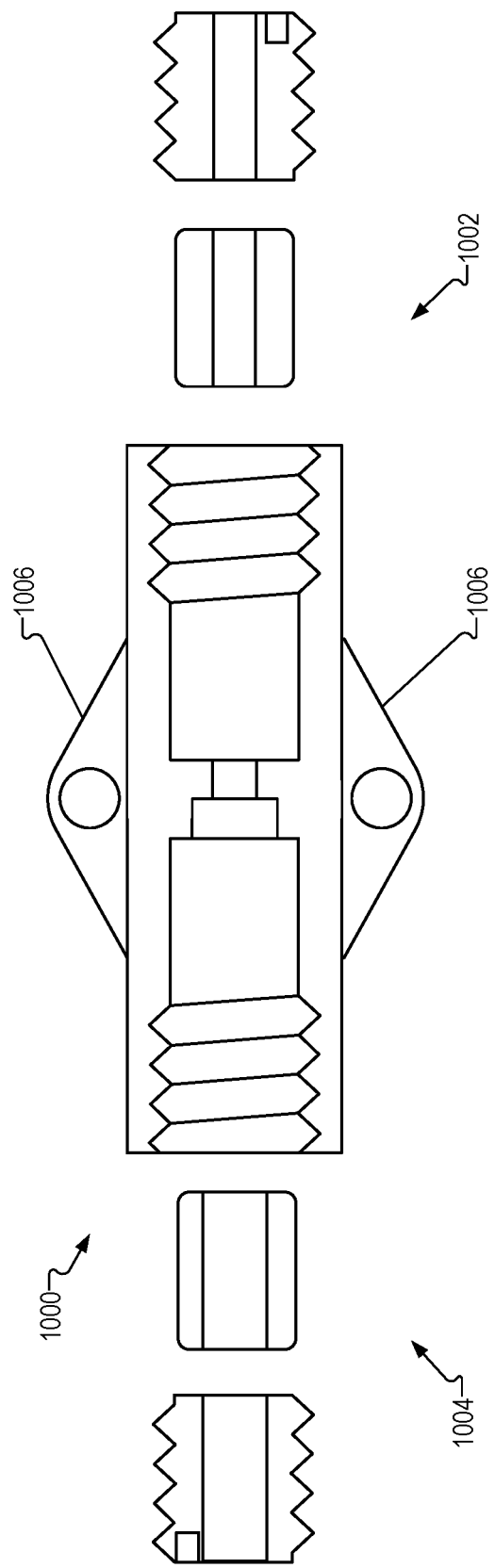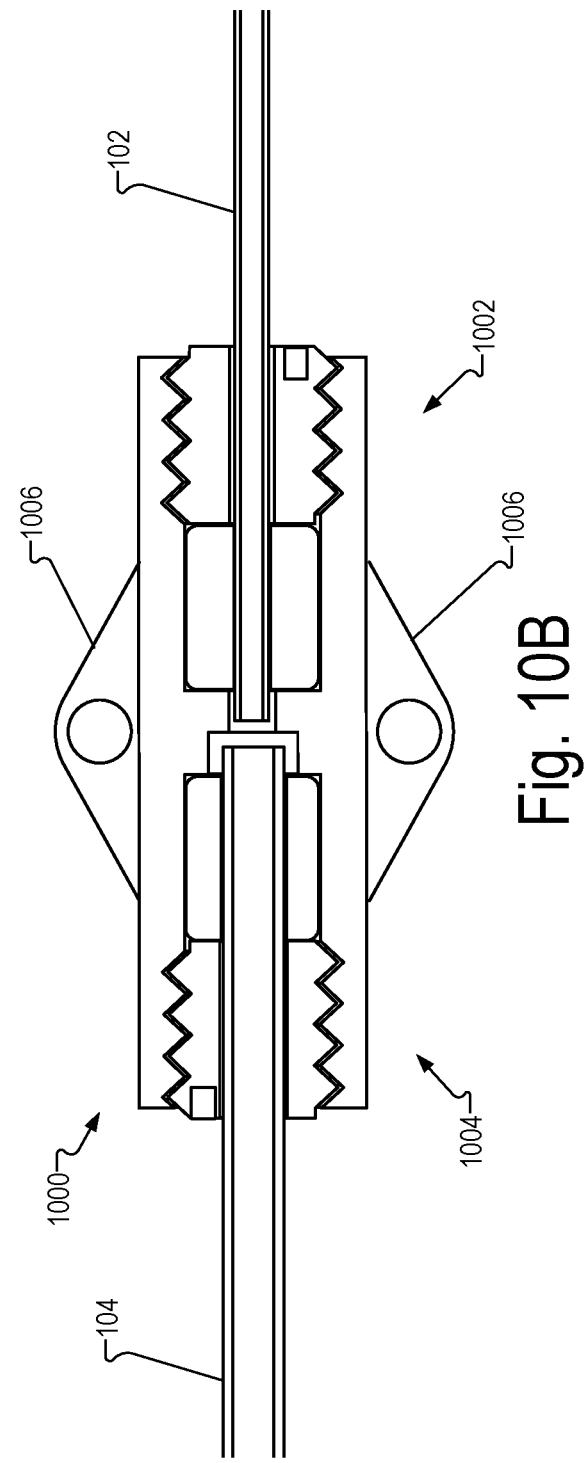
Fig. 10A
Fig. 10B

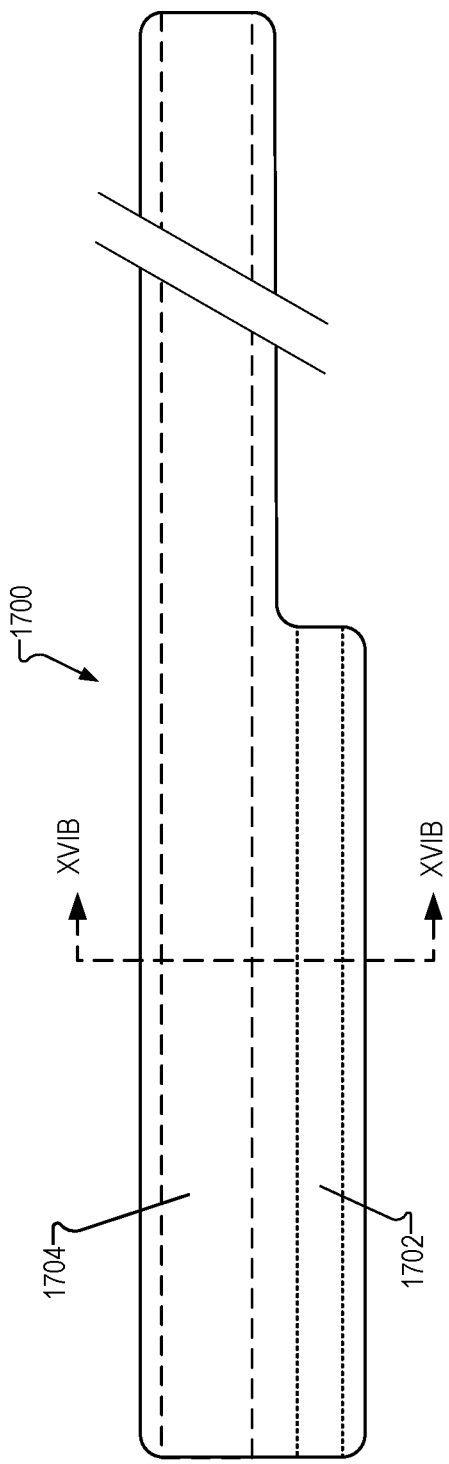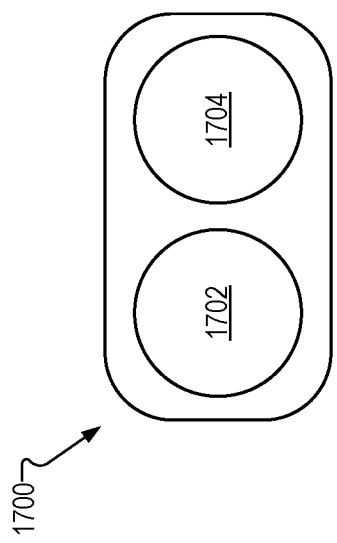

IMPLANTABLE DRUG DELIVERY SYSTEMS, ASSEMBLIES, AND METHODS

RELATED APPLICATIONS

The present application claims priority under 35 U.S.C. § 119(e) to U.S. Provisional Patent Application No. 63/219,744, filed on Jul. 8, 2021, which is incorporated herein by reference in its entirety.

BACKGROUND INFORMATION

Some people suffering from neurological disorders and other conditions may be treated with drugs, such as neurotherapeutic drugs. The drugs are often administered to the recipient intravenously, but intravenous administration often has drawbacks. For example, the blood-brain barrier may prevent effective transport of neurotherapeutic drugs to a target location in brain tissue. Additionally, intravenous administration of drugs may cause various systemic side effects for a recipient, such as in the cardiovascular system and/or the gastrointestinal system. Accordingly, there is a need for more effective systems and methods of delivering drugs to a target location within a body of a recipient with fewer side effects for the recipient.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 8A shows a cross-sectional side view of a microcatheter and an illustrative implementation of a connector for the microcatheter in an unassembled state.

FIG. 8B shows a cross-sectional side view of the connector and microcatheter of FIG. 8A in an assembled state.

FIG. 10A shows a cross-sectional view of an illustrative implementation of a coupling that may implement the connection assembly included in the implantable drug delivery system of FIG. 1.

FIG. 10B shows a cross-sectional view of the coupling of FIG. 10A in an assembled state connected to a microcatheter and a source catheter.

FIG. 17A shows a side view of an illustrative implementation of a dual lumen catheter that may implement the microcatheter of the drug delivery system of FIG. 1.

FIG. 17B shows a cross-sectional view of the dual lumen catheter of FIG. 17B.

DETAILED DESCRIPTION

Implantable drug delivery systems, assemblies, and methods are described herein. For example, an illustrative implantable drug delivery system may include a connection assembly, a source catheter, and a microcatheter. A proximal end portion of the source catheter may be configured to be fluidically connected to a fluid source configured to provide a fluid (e.g., a neurotherapeutic drug). A distal end portion of the source catheter may be configured to be fluidically connected to the connection assembly. The microcatheter may include a proximal end portion configured to be fluidically connected to the connection assembly. A distal end portion of the microcatheter may include an elution opening configured to elute the fluid to a target location (e.g., a brain) within a recipient. As described herein, the fluid source may be configured to provide the fluid to the target location by way of the source catheter, the microcatheter, and the connection assembly, which fluidically connects the source catheter to the microcatheter.

As used herein, the source catheter and the microcatheter may be "fluidically connected" one to another by being coupled such that fluid may flow from the source catheter to the microcatheter. For example, an illustrative connection assembly may comprise a cranial port that includes a base member configured to be attached to a skull of the recipient and a manifold on the base member. The proximal end portion of the microcatheter and the distal end portion of the source catheter may be connected to the manifold. Thus, the fluid source and source catheter, which may be physically dissimilar (e.g., in shape, robustness, stiffness, etc.) from the microcatheter, may be fluidically connected to the microcatheter through the manifold of the cranial port.

Because the cranial port is anchored to the skull and the source catheter and the microcatheter are fluidically connected through the cranial port, mechanical forces that might act on the microcatheter are reduced or prevented. Thus, the cranial port helps secure the position of the implanted microcatheter at the target location and prevents dislocation of the implanted distal end of the microcatheter.

Various embodiments of implantable drug delivery systems, assemblies, and methods will now be described in more detail with reference to the figures.

Figure 1:
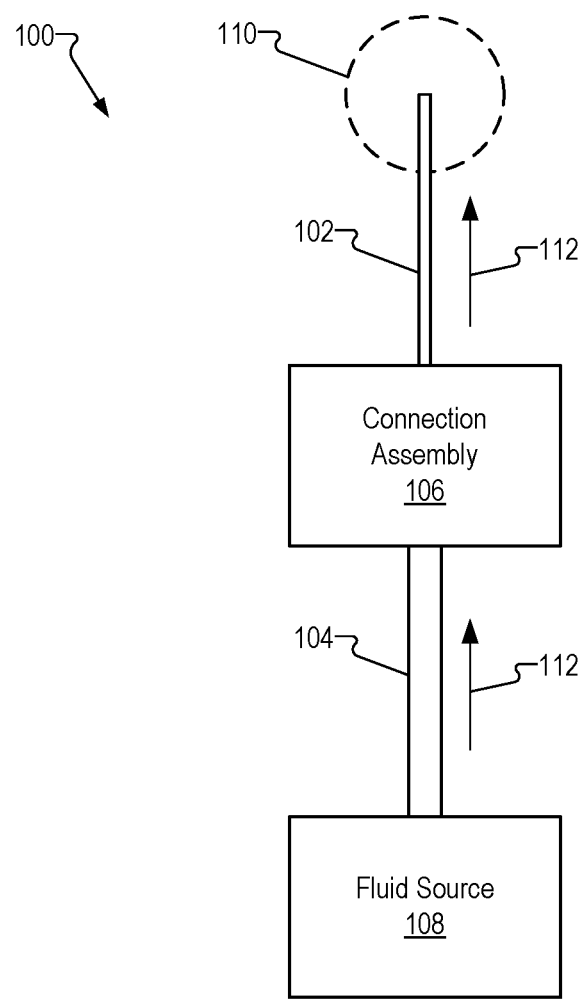
FIG. 1 shows a functional diagram of an illustrative implantable drug delivery system.

FIG. 1 shows a functional diagram of an illustrative implantable drug delivery system 100 ("system 100"). FIG. 1 shows system 100 in an assembled state, such as after system 100 has been implanted in a recipient. However, system 100 may also be in an unassembled state, such as prior to implantation in the recipient. While in the unassembled state, one or more components of system 100 may be unconnected from other components of the system.

As shown in FIG. 1, system 100 includes a microcatheter 102, a source catheter 104, a connection assembly 106 (e.g., a cranial port) for fluidically connecting microcatheter 102 and source catheter 104, and a fluid source 108 (e.g., a fill port) configured to provide a fluid. The fluid may include, for example, a drug (e.g., a neurotherapeutic drug), a rinse (e.g., a saline solution), water, or any other fluid. System 100 may also include additional or alternative components (not shown) as may serve a particular implementation (e.g., bone screws, a pump, a syringe, a non-coring needle, etc.).

A distal end portion of microcatheter 102 is configured to be implanted at a target location 110 within the recipient. As used herein, a "recipient" may include a body of a live human or animal, a human or animal cadaver, a portion of human or animal anatomy, tissue removed from human or animal anatomies, non-tissue work pieces, a training model, a dummy, etc. In some examples, target location 110 is a brain of the recipient and the fluid includes a neurotherapeutic drug. For example, the distal end portion of microcatheter 102 may be implanted in parenchymal tissue (e.g., nervous tissue) of the brain to deliver the neurotherapeutic drug directly to the parenchymal tissue, thereby bypassing the blood-brain barrier and the cardiovascular system. Any one or more additional components of system 100 may also be implantable in the recipient. For example, connection assembly 106 may be implantable on a skull of the recipient, fluid source 108 may be implantable in the thorax of the recipient, and/or source catheter 104 may be implantable in the recipient extending from the thorax to the skull. System 100 is configured to deliver the fluid from fluid source 108 to target location 110 through source catheter 104, connection assembly 106, and microcatheter 102, as indicated by arrows 112.

As used herein, "distal" means located away from fluid source 108 in a direction of fluid flow through system 100 (as indicated by arrows 112), and "proximal" means located nearer fluid source 108. For example, as shown in FIG. 1 a distal end portion of microcatheter 102 is implantable at target location 110 and a proximal end portion of microcatheter 102 is connected to connection assembly 106. Additionally, a distal end portion of source catheter 104 is connected to connection assembly 106 and a proximal end portion of source catheter 104 is connected to fluid source 108.

Illustrative embodiments of microcatheter 102, source catheter 104, connection assembly 106, and fluid source 108 will now be described.

Microcatheter 102 includes a flexible, hollow tube configured to be implanted at target location 110 to deliver the fluid to tissue at target location 110. Microcatheter 102 may be formed of any suitable material, such as polyurethane, silicone, and/or any other biocompatible material. Microcatheter 102 may be soft and flexible to prevent injury to surrounding tissue and to facilitate implantation at target location 110. In some examples, the hardness of microcatheter 102 is about 70 Shore A durometer or less. In further examples, the hardness of microcatheter 102 is between about 20 Shore A and about 60 Shore A durometer. In yet further examples, the hardness of microcatheter 102 is between about 30 Shore A and about 50 Shore A durometer. In some examples, such as when target location 110 is in the brain, microcatheter 102 is softer than the surrounding tissue to prevent injury to the surrounding tissue.

The hardness and flexibility of microcatheter 102 may also depend on the wall thickness of microcatheter 102. In some examples, the wall thickness of microcatheter 102 is between about 0.05 mm and about 0.15 mm. In other examples, the wall thickness of microcatheter 102 is between about 5% and about 30% of the outer diameter of microcatheter 102. In yet further examples, the wall thickness of microcatheter 102 is between about 7% and about 20% of the outer diameter of microcatheter 102. In other examples, the wall thickness of microcatheter 102 is between about 10% and about 15% of the outer diameter of microcatheter 102.

Microcatheter 102 may have any suitable outer diameter and/or inner diameter as may serve a particular implementation. In some examples, the outer diameter of microcatheter 102 is about 1.0 millimeter (mm) or less. In further examples, the outer diameter of microcatheter 102 is between about 0.50 mm and about 1.0 mm. In some examples, the inner diameter of microcatheter 102 is between about 0.30 mm and about 0.80 mm. Generally, the length of microcatheter 102 depends on where the distal end portion will be implanted (e.g., the implantation depth in brain tissue, the thickness of the skull, etc.) and the distance from target location 110 to connection assembly 106. Accordingly, microcatheter 102 may be cut to a desired length during implantation.

Microcatheter 102 includes an elution opening through which the drug elutes from microcatheter 102. In some embodiments, the elution opening may be a distal tip of microcatheter 102. To prevent the buildup of protein and other particles in microcatheter 102 caused by the backflow of ambient fluid (e.g., cerebrospinal fluid (CSF)) into microcatheter 102 through the elution opening, the distal tip may include a one-way valve, such as a duckbill valve. However, forming a duckbill valve at the distal tip may be difficult with the small dimensions of microcatheter 102. Accordingly, in other embodiments the elution opening is provided on a side wall of microcatheter 102, and a one-way valve is provided over the elution opening, as will now be described with reference to FIG. 2.

Figure 2:
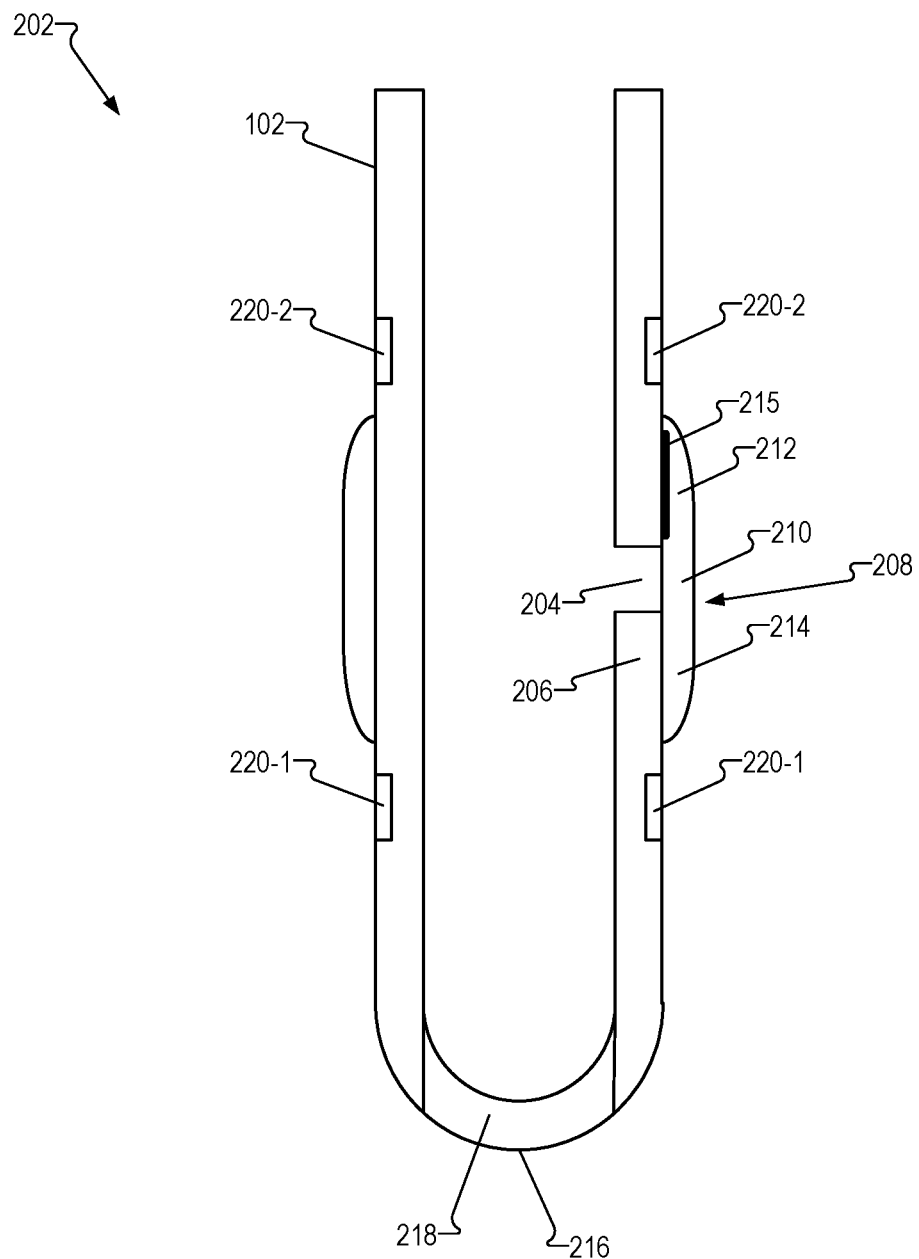
FIG. 2 shows a cross-sectional view of a distal end portion of an illustrative implementation of a microcatheter included in the implantable drug delivery system of FIG. 1.

FIG. 2 shows a cross-sectional view of a distal end portion 202 of an illustrative implementation of microcatheter 102. As shown in FIG. 2, a hole 204 is formed in a side wall 206 of distal end portion 202 of microcatheter 102. Hole 204 may have any suitable size and shape. In some examples, hole 204 has a diameter or width between about 0.25 mm and about 0.50 mm. In further examples, hole 204 has a diameter or width between about 50% and about 90% of the inner diameter of microcatheter 102. While FIG. 2 shows a single hole 204, microcatheter 102 may have any other number of holes 204 positioned at any suitable locations.

To prevent the backflow of ambient fluid into microcatheter 102 through hole 204, microcatheter 102 includes a one-way valve 208 at hole 204 or upstream from hole 204. In the example shown in FIG. 2, the one-way valve 208 includes a flexible, tubular sleeve 210 positioned over hole 204. Sleeve 210 may be formed of any suitable material (e.g., polyurethane or silicone), and may be the same as or different from the material used for microcatheter 102. In some examples, sleeve 210 is formed of silicone and has a hardness between about 20 Shore A and about 70 Shore A durometer.

Sleeve 210 may be formed to have a friction-fit over microcatheter 102 so that sleeve 210 does not move along microcatheter 102 once sleeve 210 is positioned over hole 204. To this end, sleeve 210 may have an inner diameter slightly smaller (e.g., within about 0.05 mm) than the outer diameter of microcatheter 102 so as to maintain a tight fit around microcatheter 102. For example, the inner diameter of sleeve 210 may be about 0.02% to about 0.05% smaller than the outer diameter of microcatheter 102, which may be sufficient to prevent backflow and still allow fluid to exit from microcatheter 102. In some examples, a proximal end portion 212 (or, alternatively, a distal end portion 214) of sleeve 210 may be a bonding area that is attached to side wall 206 by an adhesive 215 to prevent sleeve 210 from separating from side wall 206. The adhesive bonding area is not limited to proximal end portion 212 (or distal end portion 214) of sleeve 210, as sleeve 210 may be bonded to side wall 206 by an adhesive at any additional or alternative location provided that sleeve 210 may partially separate from side wall 206 to allow fluid to exit microcatheter 102.

When fluid from fluid source 108 is not pushed through microcatheter 102 so that no pressure is exerted on sleeve 210 through hole 204, sleeve 210 forms a tight seal over hole 204 and prevents backflow of ambient fluid into microcatheter 102 through hole 204, as shown in FIG. 2. When fluid from fluid source 108 is pushed through microcatheter 102, as indicated by arrow 302 shown in FIG. 3, the fluid exerts a pressure on the inner wall of sleeve 210 through hole 204 and pushes the non-adhered portion of sleeve 210 (e.g., the distal end portion 214 or the proximal end portion 212) away from side wall 206, thereby creating a small gap through which the fluid exits microcatheter 102 and enters into surrounding tissue, as indicated by arrow 304. When the fluid flow stops and the pressure drops, sleeve 210 returns to its original shape and position to seal hole 204, as shown in FIG. 2.

Figure 3:
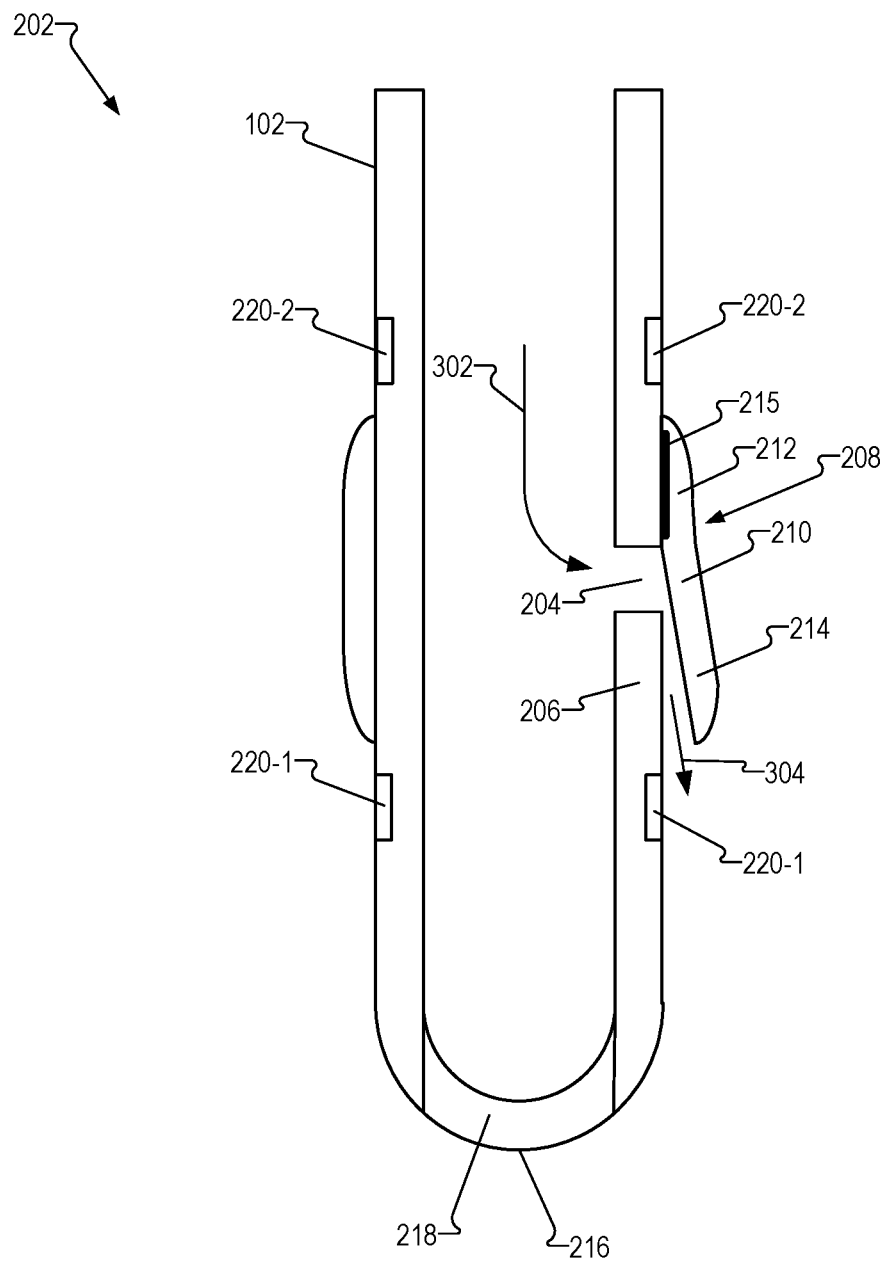
FIG. 3 shows the cross-sectional view of the distal end portion of the microcatheter of FIG. 2 when fluid from a fluid source is pushed through the microcatheter.

While FIGS. 2 and 3 show one hole 204, in other examples microcatheter 102 may have multiple holes 204 formed within side wall 206, and a single sleeve 210 may cover each of the holes 204. In alternative examples, different sleeves may be used for different holes 204.

In the examples in which the elution opening includes hole 204 within side wall 206, a distal tip 216 of microcatheter 102 may be sealed with a sealant 218 to prevent the fluid from exiting through distal tip 216 and to ensure that the fluid exits microcatheter 102 only through hole 204. Any suitable sealant may be used, such as an adhesive, silicone, or a molten polyurethane.

Figure 4:
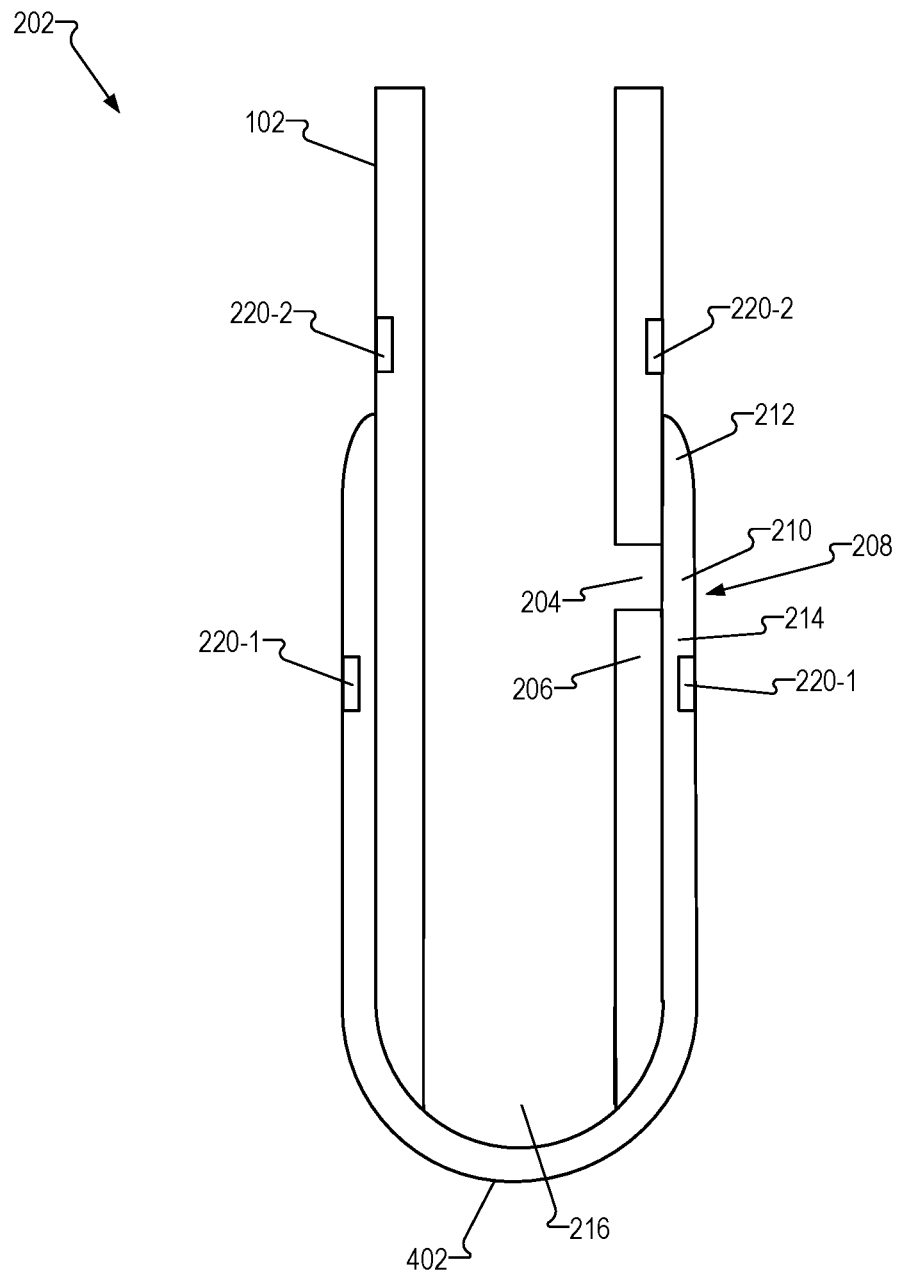
FIG. 4 shows a cross-sectional view of a distal end portion of another illustrative implementation of the microcatheter included in the implantable drug delivery system of FIG. 1.

Additionally or alternatively to using a sealant, distal tip 216 may be closed and sealed with a sleeve having a closed distal tip, as shown in FIG. 4. FIG. 4 is similar to FIG. 2 except that distal tip 216 of microcatheter 102 is not sealed with a sealant, but rather sleeve 210 has a closed distal tip 402 that covers distal tip 216. Thus, sleeve 210 seals both distal tip 216 and hole 204. In some embodiments, sleeve 210 may be secured to the distal end portion 202 of microcatheter 102 with an adhesive (e.g., on a distal side of hole 204). When fluid from fluid source 108 is pushed through microcatheter 102, the friction-fit (and/or adhesive) of sleeve 210 prevents sleeve 210 from sliding off the distal end portion 202 of microcatheter 102. The fluid pushes the proximal end portion 212 of sleeve 210 away from side wall 206, creating a small gap through which the fluid may exit microcatheter 102 and enter into surrounding tissue.

A sealed distal tip 216, as in the embodiments shown in FIGS. 2-4, also enables the use of a stylet to implant microcatheter 102. For example, a stainless steel stylet having an outer diameter smaller than the inside diameter of microcatheter 102 may be inserted into microcatheter 102 to stiffen microcatheter 102 so that microcatheter 102 may be guided to the target location. The stylet may then be removed after microcatheter 102 has been implanted at the target location. In some examples, distal tip 216 or distal tip 402 may be atraumatic to minimize or prevent injury to tissue during implantation of the distal end portion of microcatheter 102. For example, as shown in FIGS. 2-4, distal tip 216 and distal tip 402 are rounded.

Microcatheter 102 may be configured to be implanted in the body under image guidance (e.g., fluoroscopy, radioscopy, etc.) and/or stereotactic guidance. For example, as shown in FIGS. 2 and 3, microcatheter 102 includes markers 220 (e.g., marker 220-1 and marker 220-2) positioned around side wall 206 on either side of hole 204. Markers 220 may be formed of a fluorescent material (e.g., indocyanine green), radiopaque material (e.g., platinum, iridium, barium sulfate, bismuth compounds, tungsten, etc.), and/or any other material that may be imaged through an alternative imaging modality (e.g., an imaging modality other than visible light imaging). Markers 220 may be embedded in, coated on, adhered to, or otherwise provided on microcatheter 102. In some examples, markers 220 include separate rings or sleeves that friction fit around microcatheter 102. In yet further examples, as shown in FIG. 4, one or more markers 220 may be provided on (e.g., embedded in, coated on, adhered to, etc.) a sleeve (e.g., sleeve 210) positioned around microcatheter 102. For example, as shown in FIG. 4, marker 220-1 is provided on sleeve 210 and marker 220-2 is provided on side wall 206. However, marker 220-2 may also be provided on sleeve 210 on the opposite side of hole 204 if marker 220-2 is sufficiently flexible to allow one-way valve 208 to open. Markers 220 may be configured to indicate a location of the elution opening (e.g., hole 204). For example, markers 220 may be positioned within a predetermined distance (e.g., within about 5 mm to about 10 mm) from hole 204 or from an open distal tip of microcatheter 102. In further examples, markers 220 may have a unique shape configured to indicate the elution opening (e.g., a ring or circle surrounding hole 204, etc.). Under image guidance, markers 220 may be used during implantation to position hole 204 at the target location. While FIGS. 2-4 show that microcatheter 102 or sleeve 210 includes two ring-like markers 220, microcatheter 102 and sleeve 210 may have any other number (e.g., one or more than two) and configuration of markers 220 as may serve a particular implementation. Alternatively, microcatheter 102 and sleeve 210 may have no markers 220.

Referring again to FIG. 1, when system 100 is implanted in the recipient microcatheter 102 is configured to receive fluid (e.g., neurotherapeutic drugs) from fluid source 108. In some embodiments, fluid source 108 may be implanted in the recipient away from target location 110. For example, target location 110 may be the brain of a recipient and fluid source 108 may be implanted in a thorax (e.g., a pectoral region) of the recipient.

Due to the soft and flexible construction of microcatheter 102, microcatheter 102 may not be physically and mechanically suitable for implantation from the head to the thorax to connect directly to the fluid source 108. For example, pulling on microcatheter 102 could damage microcatheter 102, such as by stretching, tearing, and/or constricting microcatheter 102. Furthermore, a single microcatheter 102 that extends from the head to the thorax may be damaged after implantation due to the length of microcatheter 102 and the various twists, flexions, and movements to which microcatheter 102 may be subjected during normal activity by the recipient. Moreover, a single microcatheter 102 that extends from the head to the thorax might be too long to implant with a stylet.

To prevent these issues, the proximal end portion of microcatheter 102 may be fluidically connected to the distal end portion of a more physically and mechanically robust source catheter 104 by way of connection assembly 106. Thus, a shorter, softer, and more flexible microcatheter 102 may be easily implanted with a stylet and, when fluidically connected to source catheter 104 by way of connection assembly 106, may receive fluid from fluid source 108 by way of source catheter 104 and connection assembly 106.

Figure 5A:
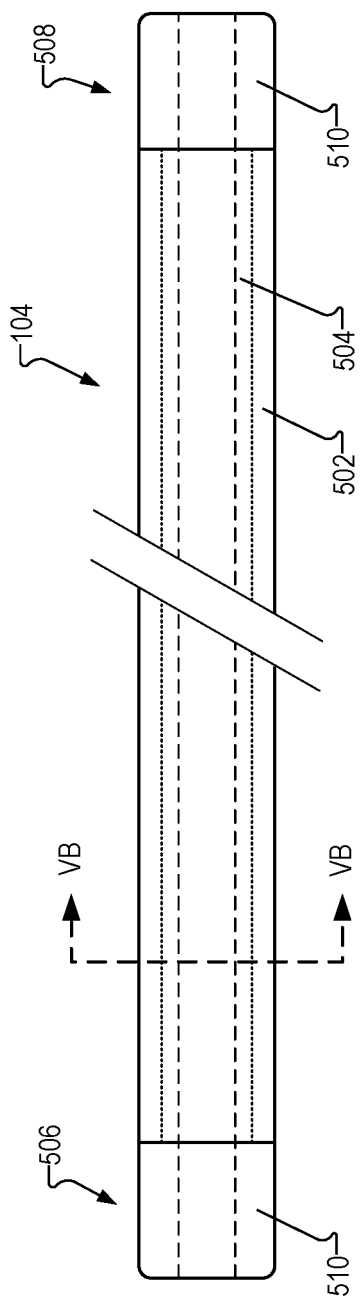
FIG. 5A shows an illustrative implementation of a source catheter included in the implantable drug delivery system of FIG. 1.
Figure 5B:
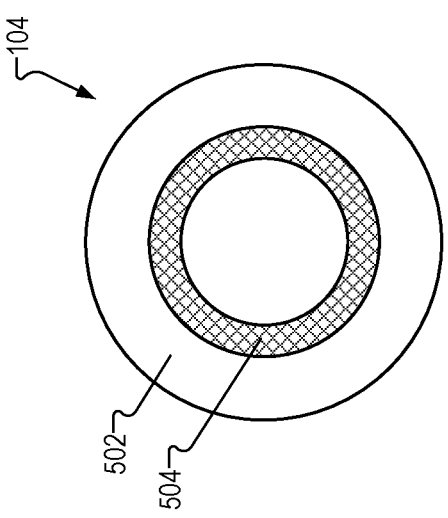
FIG. 5B shows a cross-sectional view of the source catheter of FIG. 5A.

FIGS. 5A and 5B show an illustrative implementation of source catheter 104. FIG. 5A shows a side view of source catheter 104 and FIG. 5B shows a cross-sectional view of source catheter 104 as taken along the dashed line labeled VB-VB. Source catheter 104 includes a hollow tube 502 and may be formed of any suitable material, such as polyurethane, silicone, and/or other biocompatible material. Source catheter 104 may be more physically and mechanically robust than microcatheter 102. In some examples, source catheter 104 has a hardness that is greater than the hardness of microcatheter 102. In some examples, the hardness of source catheter 104 is about 70 Shore A durometer or less. In further examples, the hardness of source catheter 104 is between about 20 Shore A and about 60 Shore A durometer. In yet further examples, the hardness of source catheter 104 is between about 30 Shore A and about 50 Shore A durometer.

In some examples, as shown in FIGS. 5A and 5B, source catheter 104 includes an inner braid 504 (e.g., a stainless steel braid) designed to resist kinking or excessive bending of source catheter 104. Braid 504 may have any suitable number of braid strands and tightness. In some examples, as shown in FIG. 5A, the distal end portion and/or proximal end portion of source catheter 104 does not include braid 504. For example, a distal end portion 506 and a proximal end portion 508 of source catheter 104 may each include a molded tip 510 to prevent fraying of the ends of braid 504. While FIGS. 5A and 5B show that source catheter 104 includes inner braid 504, in other examples source catheter 104 does not include inner braid 504.

Source catheter 104 may have any suitable wall thickness. In some examples, the wall thickness of source catheter 104 is between about 0.25 mm and about 0.50 mm. In other examples, the wall thickness of source catheter 104 is between about 10% and about 40% of the outer diameter of source catheter 104. In yet further examples, the wall thickness of source catheter 104 is between about 15% and about 35% of the outer diameter of source catheter 104. In other examples, the wall thickness of source catheter 104 is between about 20% and about 30% of the outer diameter of source catheter 104. In further examples, the wall thickness of source catheter 104 is greater than the wall thickness of microcatheter 102.

Source catheter 104 may have any suitable outer diameter and/or inner diameter as may serve a particular implementation. In some examples, the outer diameter of source catheter 104 is about 1.5 mm or less. In further examples, the outer diameter of source catheter 104 is between about 1.0 mm and about 1.5 mm. In some examples, the inner diameter of source catheter 104 is between about 0.5 mm and about 1.0 mm.

Due to the construction of source catheter 104, source catheter 104 may be physically dissimilar from microcatheter 102 in various ways, such as in material, hardness, braiding, and/or one or more size measurements (e.g., outer diameter, inner diameter, and/or wall thickness). Thus, source catheter 104 may be configured to be tunneled under skin by pulling (e.g., with a tunneling tool) without damaging source catheter 104.

Referring again to FIG. 1, connection assembly 106 is configured to fluidically connect the proximal end portion of microcatheter 102 to the distal end portion of source catheter 104, which may be larger and/or more physically and mechanically robust than microcatheter 102. Thus, microcatheter 102 may be easily implanted and, when fluidically connected to source catheter 104 by way of connection assembly 106 (e.g., a cranial port), microcatheter 102 may receive fluid from fluid source 108 by way of source catheter 104. In some examples, connection assembly 106 may also be configured to be anchored to the body, such as to bone (e.g., the skull) and/or to tissue. Thus, connection assembly 106 may also reduce or prevent application of stress or mechanical forces on microcatheter 102, such as stresses or forces transmitted from source catheter 104.

Figure 6A:
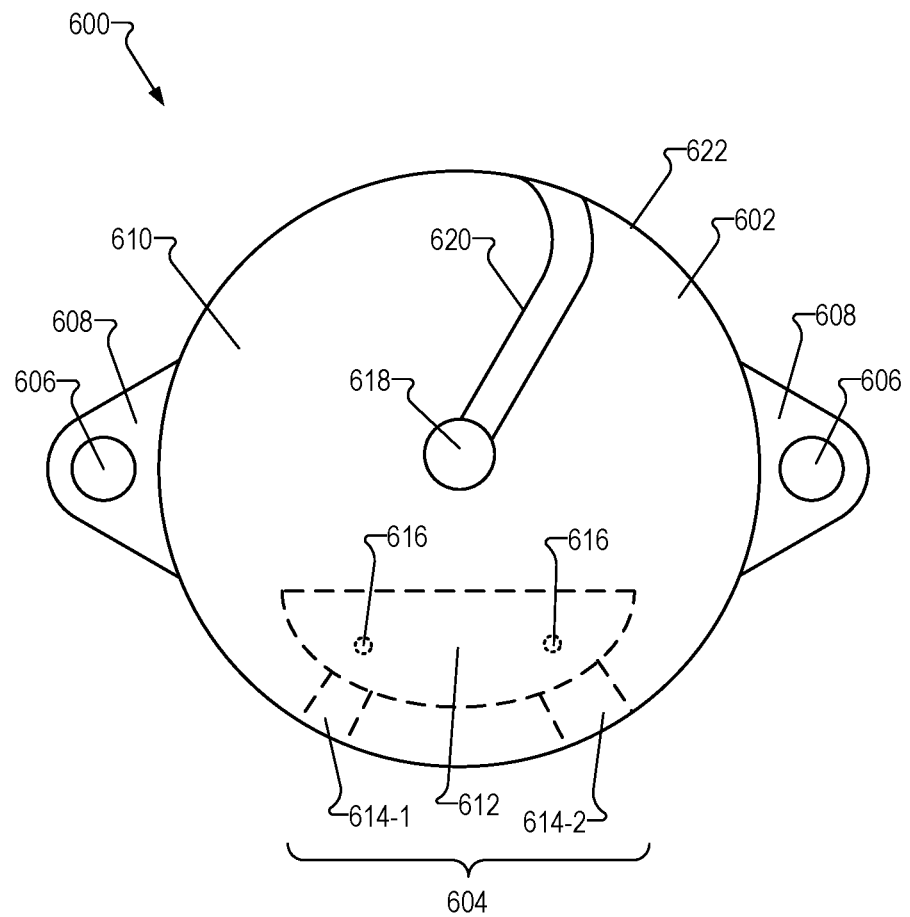
FIG. 6A shows a top view of an illustrative cranial port that may implement a connection assembly included in the implantable drug delivery system of FIG. 1.
Figure 6B:
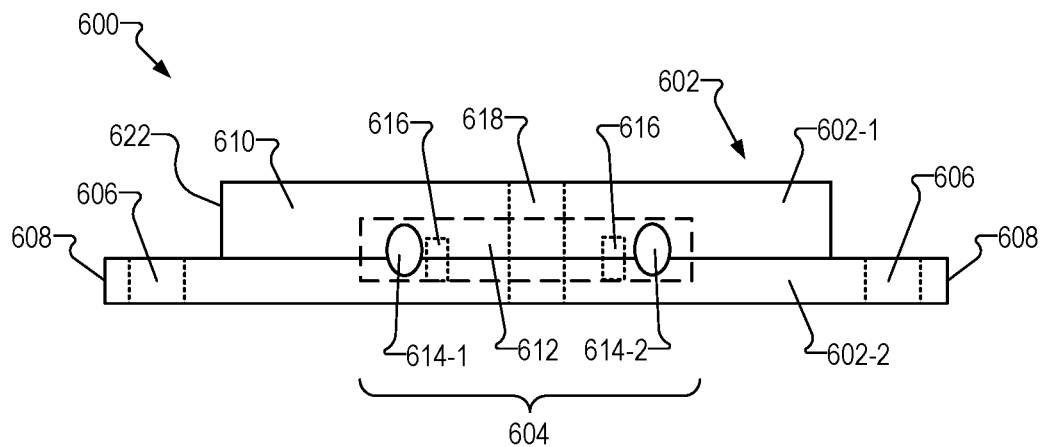
FIG. 6B shows a side view of the cranial port of FIG. 6A.
Figure 7:
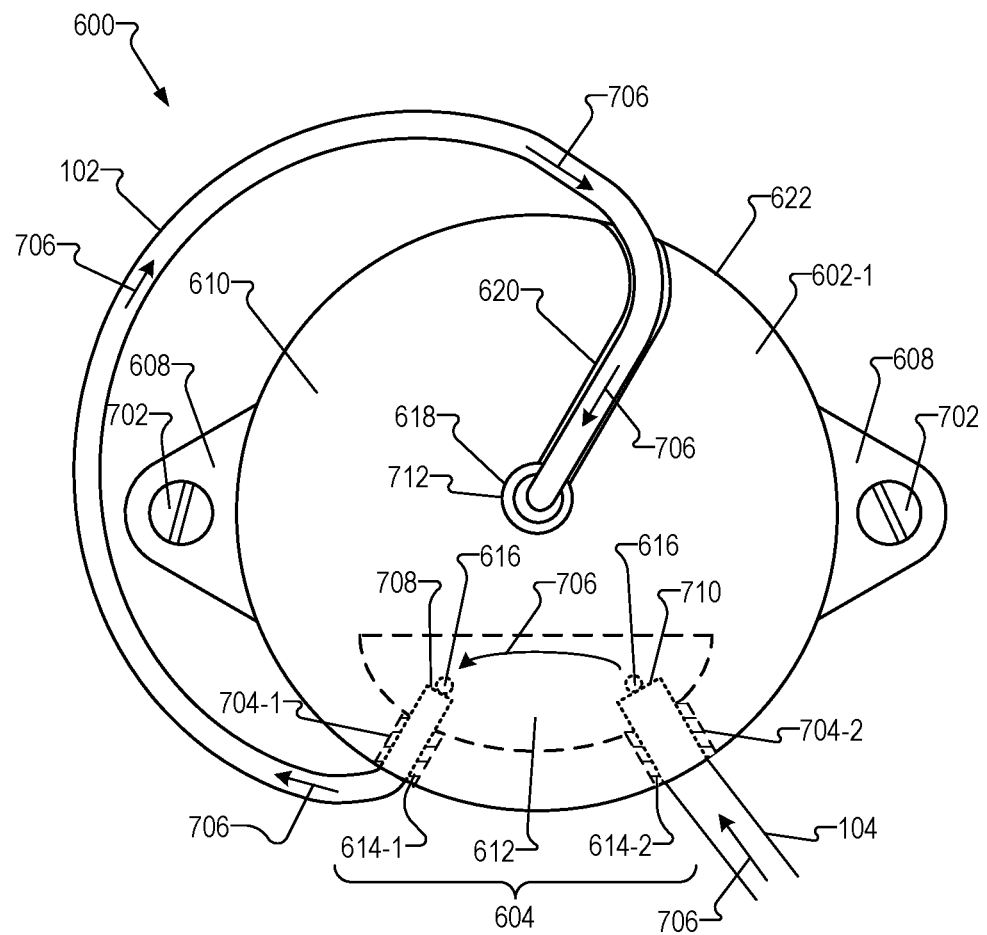
FIG. 7 shows a top view of the cranial port of FIGS. 6A and 6B when a proximal end portion of a microcatheter and a distal end portion of a source catheter are connected by way of a manifold in the cranial port.

In some examples, connection assembly is implemented by a cranial port that may be secured to the skull of the recipient. FIGS. 6A-9B show illustrative embodiments of a cranial port 600 that may implement connection assembly 106. FIG. 6A shows a top view of cranial port 600 and FIG. 6B shows a side view of cranial port 600. FIGS. 6A and 6B show cranial port 600 unconnected to microcatheter 102 and source catheter 104. As shown in FIGS. 6A and 6B, cranial port 600 includes a base member 602 and a manifold 604 through which the proximal end portion of microcatheter 102 may be fluidically connected to the distal end portion of source catheter 104. FIG. 7 shows a top view of cranial port 600 when the proximal end portion of microcatheter 102 and the distal end portion of source catheter 104 are connected to manifold 604.

Base member 602 may be formed of any suitable rigid or semi-rigid material, such as a metal (e.g., stainless steel), a hard plastic (e.g., polyethylene or polyether ether ketone (PEEK)), or a hard polymer (e.g., polyurethane). As shown, base member 602 is formed of a top plate 602-1 and a bottom plate 602-2 joined and held together, such as by an adhesive, screws, a snap-fit, a clip, or other suitable fastener. Alternatively, base member 602 may be a unitary body.

Base member 602 may be configured to be anchored to the recipient. For example, base member 602 includes two holes 606 formed in anchor tabs 608 protruding from a main portion 610, which is configured to provide structural support for microcatheter 102 and manifold 604. Anchor tabs 608 may be formed in top plate 602-1 and/or bottom plate 602-2. Holes 606 may be used to attach base member 602 to the body (e.g., to the skull or to tissue), such as by bone screws 702 (see FIG. 7), sutures, staples, and/or other fasteners. In some examples, anchor tabs 608 are formed in both top plate 602-1 and bottom plate 602-2 and bone screws (or other fasteners) through holes 606 may also fasten top plate 602-1 and bottom plate 602-2 together. While FIGS. 6A and 6B show two holes 606, base member 602 may have any other suitable number of holes 606 as may serve a particular implementation (e.g., one or more than two). Additionally or alternatively to holes 606, base member 602 may be attached to the body by an adhesive (e.g., a bone adhesive, tissue glue, etc.).

While FIGS. 6A and 6B show that base member 602 is generally circular, base member 602 may have any other suitable shape (e.g., circular, rectangular, oval, freeform, etc.). Base member 602 may also have any suitable size. In some examples, base member 602 (e.g., main portion 610) has a diameter or width between about 10 mm and about 25 mm. Base member 602 (e.g., main portion 610) may have a thickness between about 3 mm and about 5 mm. Thus, cranial port 600 may have a low profile and little to no cosmetic appearance when implanted in the recipient.

Manifold 604 includes a hollow chamber 612 with a first opening 614-1 for connection with microcatheter 102 and a second opening 614-2 for connection with source catheter 104 (collectively referred to as "openings 614"). As shown, manifold 604 may be formed integrally with base member 602. Manifold 604 and openings 614 may be formed by forming wells or cavities in top plate 602-1 and/or bottom plate 602-2 and then joining top plate 602-1 and bottom plate 602-2. An adhesive and/or a sealer, such as an O-ring (not shown) may be positioned between top plate 602-1 and bottom plate 602-2 and around the wells or cavities to prevent fluid leakage between top plate 602-1 and bottom plate 602-2 when cranial port 600 is implanted in the recipient. In alternative embodiments, base member 602 may be formed as a unitary body, such as by additive manufacturing or by removing material through openings 614. In yet further examples, manifold 604 may be formed separately and attached to base member 602, such as by mechanical fastener or adhesive.

As shown in FIG. 7, microcatheter 102 may be fluidically connected to manifold 604 through first opening 614-1 by way of a first connector 704-1, and source catheter 104 may be fluidically connected to manifold 604 through second opening 614-2 by way of a second connector 704-2 (collectively referred to as "connectors 704"). Connectors 704 may have a similar construction, potentially differing in size in some embodiments based on the sizes of microcatheter 102 and source catheter 104. Since microcatheter 102 and source catheter 104 are each fluidically connected to manifold 604, microcatheter 102 and source catheter 104 are fluidically connected to one another through manifold 604.

FIGS. 8A and 8B show an illustrative implementation of connector 704-1 for microcatheter 102. FIG. 8A shows a cross-sectional side view of connector 704-1 and microcatheter 102 in an unassembled state, and FIG. 8B shows a cross-sectional side view of connector 704-1 in an assembled state with microcatheter 102. It will be understood that connector 704-2 for source catheter 104 may have a similar construction, although "distal" and "proximal" descriptors may be reversed as appropriate. Accordingly, description of connector 704-2 will be omitted. As shown in FIGS. 8A and 8B, connector 704-1 includes an outer member 802, a sealing member 804, and a pressing member 806.

Outer member 802 is a rigid or semi-rigid hollow tube having an inner channel 808, a proximal end wall 810, and an open distal end 812. Outer member 802 is configured to fit into opening 614-1 of manifold 604. Accordingly, outer member 802 may be sized and shaped to substantially match a size and shape of opening 614-1. For example, where opening 614-1 is cylindrical, an outside shape of outer member 802 may also be cylindrical. Outer member 802 may be secured to side walls of opening 614-1 with an adhesive to seal any gaps between outer member 802 and the side walls of opening 614-1. Alternatively, outer member 802 may be formed integrally with base member 602. Inner channel 808 includes a proximal inner portion 808-1 and a distal inner portion 808-2 in which sealing member 804 and/or pressing member 806 may be positioned. Proximal end wall 810 has an opening 814 through which a proximal end portion 816 of microcatheter 102 may be inserted when microcatheter 102 is connected to connector 704-1. In some examples, a size of opening 814 is about equal to the outer diameter of microcatheter 102. Open distal end 812 is open to allow sealing member 804 and/or pressing member 806 to be inserted into inner channel 808. In some examples, outer member 802 has a length between about 4 mm and about 8 mm. In further examples, inner channel 808 has a diameter or width of about 0.5 mm to about 1 mm.

Sealing member 804 is formed of a resilient material (e.g., silicone) and has an inner channel 818 through which proximal end portion 816 of microcatheter 102 may be inserted when microcatheter 102 is connected to connector 704-1. In some examples, sealing member 804 has a hardness between about 20 Shore A durometer and about 50 Shore A durometer. Sealing member 804 is configured to be positioned in proximal inner portion 808-1 with minimal gaps or voids between sealing member 804 and outer member 802. In some examples, sealing member 804 is sized and shaped to substantially match a size and shape of inner channel 808 (e.g., proximal inner portion 808-1). For example, where inner channel 808 is cylindrical, sealing member 804 may also be cylindrical.

Pressing member 806 is configured to press against sealing member 804 to compress sealing member 804 between pressing member 806 and proximal end wall 810. The pressure applied to sealing member 804 squeezes sealing member 804 around the proximal end portion 816 of microcatheter 102 and against outer member 802, thereby creating a watertight seal to prevent leakage of fluid through opening 814. Sealing member 804 also forms a tight hold on microcatheter 102 to prevent disconnection of microcatheter 102 from connector 704-1 but does so without limiting patency of microcatheter 102. Pressing member 806 may be formed of any suitable material that is harder than sealing member 804. For example, pressing member 806 may be formed of a hard plastic (e.g., PEEK), a hard polymer (e.g., polyurethane), or a metal (e.g., stainless steel).

Pressing member 806 may have any suitable configuration and may operate in any suitable manner. In some examples, as shown in FIGS. 8A and 8B, pressing member 806 includes a threaded retainer screw configured to be positioned in distal inner portion 808-2, which is also threaded to match the retainer screw. The retainer screw includes an inner channel 820 through which the proximal end portion 816 of microcatheter 102 may be inserted.

A distal end surface 822 of the retainer screw includes an engagement member that may be used to tighten the retainer screw when the proximal end portion 816 of microcatheter 102 is positioned through inner channel 818 and inner channel 820. As shown, the engagement member includes a socket 824 in distal end surface 822 of the retainer screw. The retainer screw may be tightened by inserting a tool into socket 824 and using the tool to apply leverage from within socket 824 to rotate the retainer screw within distal inner portion 808-2 of outer member 802 of connector 704-1. For example, such a tool may be configured to be placed around outer member 802, the tool including an attached rod which may be positioned within socket 824, so that outer member 802 and the tool body can be used in concert to apply the leverage to rotate the retainer screw. In alternative embodiments, the engagement member may be a ridge or protrusion that rises above distal end surface 822 of the retainer screw and can be grasped by a tool to be pulled or pushed and thereby rotate the retainer screw. In other embodiments, the engagement member may include one or more holes extending from a radially outer surface of pressing member 806 towards inner channel 820 and a tool having an extended portion can be inserted into the one or more holes to provide an accessible surface which can be grasped at the extended portion to rotate the retainer screw.

Pressing member 806 may have a configuration other than a retainer screw. For example, pressing member 806 may include a lid (with an opening for microcatheter 102 to pass through) that attaches (e.g., by a snap fit or threaded fit) to outer member 802 and presses directly against sealing member 804. In other examples, pressing member 806 may be a non-threaded hollow rigid body or semi-rigid body positioned within distal inner portion 808-2 and held in place, such as by a snap-fit or a lid (with an opening for microcatheter 102 to pass through) over distal end 812 of outer member 802.

As mentioned, outer member 802 may be secured in opening 614-1 with an adhesive. Microcatheter 102 may be connected to manifold 604 by inserting sealing member 804 and pressing member 806 into inner channel 808 of outer member 802 with opening 814, inner channel 818, and inner channel 820 aligned axially. The proximal end portion 816 of microcatheter 102 may be inserted through pressing member 806, sealing member 804, and then opening 814. Alternatively, microcatheter 102 may first be inserted through pressing member 806 and sealing member 804, and then the assembly may be inserted into inner channel 808 of outer member 802. Pressing member 806 may be engaged (e.g., the retainer screw may be tightened) to press against sealing member 804 and thus cause sealing member 804 in turn to press against microcatheter 102, proximal end wall 810 of outer member 802, and an inner wall of inner chamber 808 of outer member 802, which holds microcatheter 102 in position and also creates a seal against fluid traversing around microcatheter 102 within outer member 802.

The distal end portion of source catheter 104 may also be connected to manifold 604 in a manner similar to which the proximal end portion of microcatheter 102 is connected to manifold 604. When microcatheter 102 and source catheter 104 are connected to manifold 604, as shown in FIG. 7, manifold 604 of cranial port 600 acts as a fluid interface through which microcatheter 102 is fluidically connected with source catheter 104 so that fluid may flow from source catheter 104 into chamber 612 and then through microcatheter 102, as indicated by arrows 706. By indirectly connecting microcatheter 102 to source catheter 104 by way of manifold 604, forces from source catheter 104 (e.g., tugging, twisting, jolting, etc.) are minimized or inhibited from being transferred to microcatheter 102.

To prevent a proximal end 708 of microcatheter 102 and a distal end 710 of source catheter 104 from being pushed too far into chamber 612, manifold 604 may include stoppers 616 formed inside chamber 612 near openings 614. The stoppers may be protrusions formed integrally with top plate 602-1 and/or bottom plate 602-2 or may be formed separately and attached to top plate 602-1 and/or bottom plate 602-2. Additionally or alternatively to stoppers 616, openings 614 may be angled relative to chamber 612 so that proximal end 708 of microcatheter 102 and distal end 710 of source catheter 104 can be pushed far into chamber 612 without hitting a chamber wall. In other examples, a sleeve having an outer diameter greater than the diameter of inner channel 820 of pressing member 806 (or inner channel 818 of sealing member 804) may be placed over the outside of the proximal end portion of microcatheter 102 to prevent proximal end 708 of microcatheter 102 from being pushed in too far. That is, the sleeve is too large to fit at some point inside connector 704-1 and thus connector 704-1 itself acts as a stopper. A similar sleeve may also be used over the outside of the distal end portion of source catheter 104 to prevent distal end 710 of source catheter 104 from being pushed in too far.

Referring to FIGS. 6A, 6B, and 7, base member 602 may also be configured to minimize or prevent stresses and forces that might be applied to microcatheter 102. For example, as shown in FIGS. 6A and 6B, base member 602 includes an access hole 618 and a guide channel 620. Access hole 618 is a hole through base member 602 through which the distal end of microcatheter 102 may be inserted for implantation at the target location. For example, access hole 618 may provide access to a burr hole 712 in the skull, as shown in FIG. 7. Access hole 618 may be any size and shape as may serve a particular implementation.

Guide channel 620 extends from access hole 618 to an outside edge 622 of base member 602. As shown in FIGS. 6A and 7, guide channel 620 is an open channel (e.g., a groove) formed in a surface of base member 602, but guide channel 620 may alternatively be a closed channel (e.g., a tube). Guide channel 620 is configured to hold microcatheter 102 in place and limit movement of microcatheter 102 near access hole 618 to prevent dislocation of the implanted distal end of microcatheter 102. For example, guide channel 620 may have a width approximately equal to the outer diameter of microcatheter 102. To hold microcatheter 102 in place, guide channel 620 may be configured such that microcatheter 102 may be "snapped" into place in guide channel 620 and prevented from separating from guide channel 620. In an alternative embodiment, cranial port 600 may include a cover (see FIG. 9B) that may be placed over base member 602 to further restrict movement of microcatheter 102 and to protect various components of cranial port 600.

The proximal end of guide channel 620 may be positioned at any location relative to opening 614-1 of cranial port 600. In some examples, the proximal end of guide channel 620 is positioned directly across (e.g., 180°) from opening 614-1 of cranial port 600 to maximize the distance microcatheter 102 is wrapped around base member 602. In other examples, the proximal end of guide channel 620 may be positioned less than 180° or more than 180° from opening 614-1 of cranial port 600 (e.g., at 210°, 135°, 90°, 45°, etc.).

As shown in the embodiment of FIG. 7, microcatheter 102 wraps loosely around (e.g., may not be in contact with) base member 602. In other examples, microcatheter 102 may be wrapped tightly around outside edge 622 of base member 602 or over base member 602.

By the use of the cranial port 600 fixed to the skull to hold microcatheter 102 firmly in position within guide channel 620 and to connect microcatheter 102 and source catheter 104 through respective connectors 704-1 and 704-2 into manifold 604 without direct physical connection between microcatheter 102 and source catheter 104, microcatheter 102 may be partially or substantially mechanically isolated from external forces. For example, movement of a portion of microcatheter 102 extending between access hole 618 and first opening 614-1 may be isolated from disturbing a portion of microcatheter 102 extending within the skull by microcatheter 102 being held in position within guide channel 620 and by cranial port 600 being fixed to the skull. For another example, movement of source catheter 104 may be isolated from disturbing the portion of microcatheter 102 extending within the skull by source catheter 104 being positioned in second connector 704-2, by source catheter 104 being physically distanced from microcatheter 102 by the fluidic coupling through manifold 604, by microcatheter 102 being held in position within guide channel 620, and by cranial port 600 being fixed to the skull. In general, the portion of microcatheter 102 extending within the skull may be protected in several ways from movement within the skull which, absent the cranial port 600, might otherwise occur due to application of external forces.

Figure 9A:
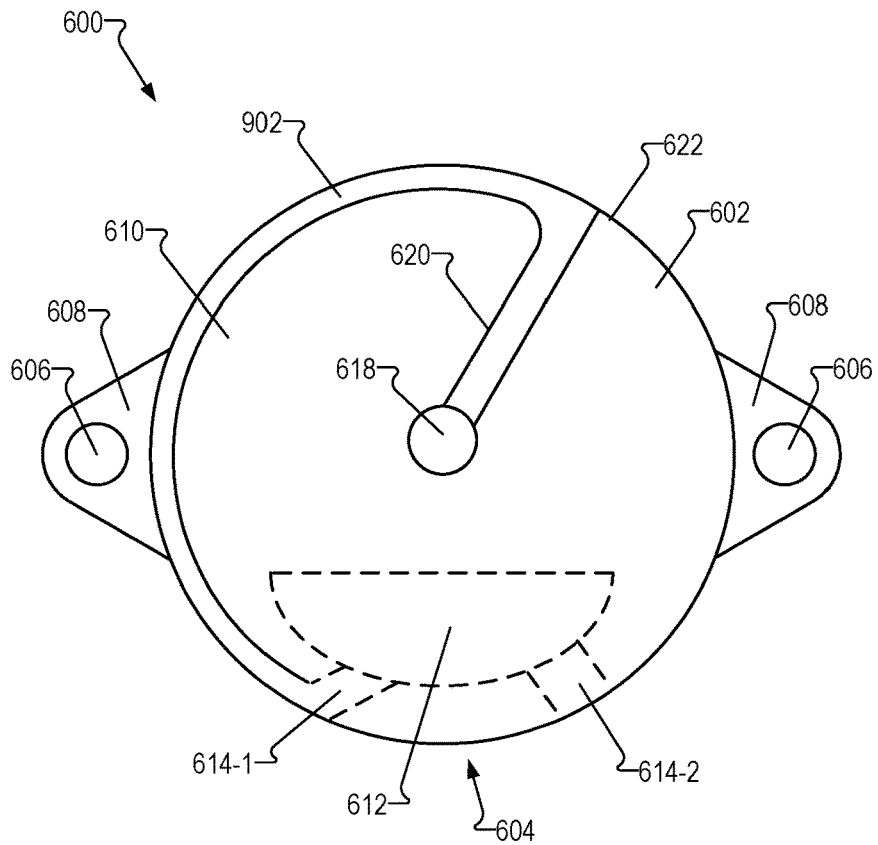
FIG. 9A shows a top view of another illustrative implementation of a cranial port that may implement the connection assembly included in the implantable drug delivery system of FIG. 1.

FIG. 9A shows a top view of another illustrative implementation of cranial port 600. FIG. 9A is similar to FIG. 6A except that in FIG. 9A, cranial port 600 includes an outer guide channel 902 towards outside edge 622 of base member 602 in which microcatheter 102 may be secured. Outer guide channel 902 may be configured similarly to guide channel 620. Outer guide channel 902 may connect to opening 614-1. In some examples, outer guide channel 902 is deep enough so that microcatheter 102 does not protrude from outside edge 622 of base member 602 or above an upper surface of base member 602.

Figure 9B:
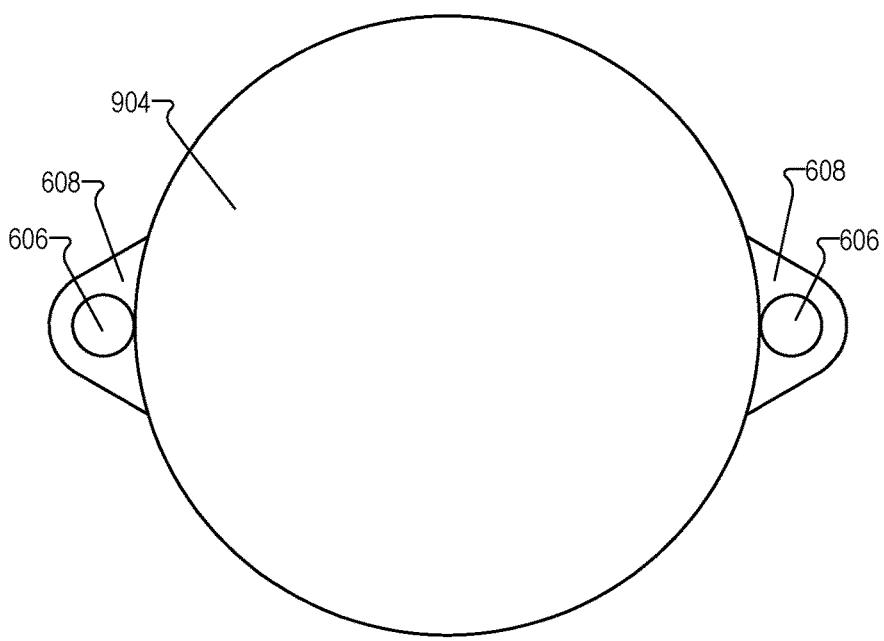
FIG. 9B shows a top view of a cover configured to cover the cranial port of FIGS. 6A, 6B, 7, and 9A.

FIG. 9B shows a top view of an optional cover 904 covering cranial port 600 shown in FIGS. 6A, 6B, 7, and 9A. Cover 904 is configured to cover a top surface and outside edge 622 of base member 602. Cover 904 may be attached to base member 602 in any suitable way, such as by a fastener, a snap-fit, a threaded fit, and/or an adhesive. When placed over base member 602 of FIG. 9A, cover 904 may also cover outer guide channel 902 to protect microcatheter 102 and prevent separation of microcatheter 102 from outer guide channel 902. Thus, cover 904 may completely cover microcatheter 102 so that no part of microcatheter 102 is exposed outside of cover 904. Cover 904 may include an opening (not shown in FIG. 9B) corresponding to opening 614-2 so that source catheter 104 may connect to manifold 604 through cover 904.

In the examples described above, connection assembly 106 (see FIG. 1) is implemented by cranial port 600. In alternative examples, connection assembly 106 may be implemented by a coupling that directly connects the proximal end of microcatheter 102 with the distal end of source catheter 104. For example, FIGS. 10A and 10B show another illustrative implementation of connection assembly 106. As shown, connection assembly 106 is implemented by a coupling 1000. FIG. 10A shows coupling 1000 in an unassembled state and FIG. 10B shows coupling 1000 in an assembled state connected to microcatheter 102 and source catheter 104.

Coupling 1000 includes a microcatheter connector 1002 and a source catheter connector 1004 connected end-to-end. Connectors 1002 and 1004 are similar to connectors 704-1 and 704-2 and therefore will not be described in detail. In some examples, outer members of connectors 1002 and 1004 are formed as a unitary body, as shown in FIGS. 10A and 10B. Alternatively, outer members of connectors 1002 and 1004 are formed separately and joined together, such as by an adhesive, snap-fit, a fastener, a threaded fit, or other suitable attachment. In some examples, as shown in FIGS. 10A and 10B, coupling 1000 includes anchor tabs 1006 so that coupling 1000 may be attached to the body (e.g., to bone).

In alternative embodiments, such as when microcatheter 102 and source catheter 104 have a similar size, microcatheter 102 and source catheter 104 may be connected directly, such as by an adhesive between a proximal tip of microcatheter 102 and a distal tip of source catheter 104. However, a direct connection may not be suitable in certain cases where microcatheter 102 and source catheter 104 are physically dissimilar and/or where source catheter 104 may exert stresses or forces on microcatheter 102.

Referring again to FIG. 1, the proximal end of source catheter 104 is connected to fluid source 108. Fluid source 108 may be implanted in the body, such as in the pectoral fascia between the skin and muscle.

Figure 11A:
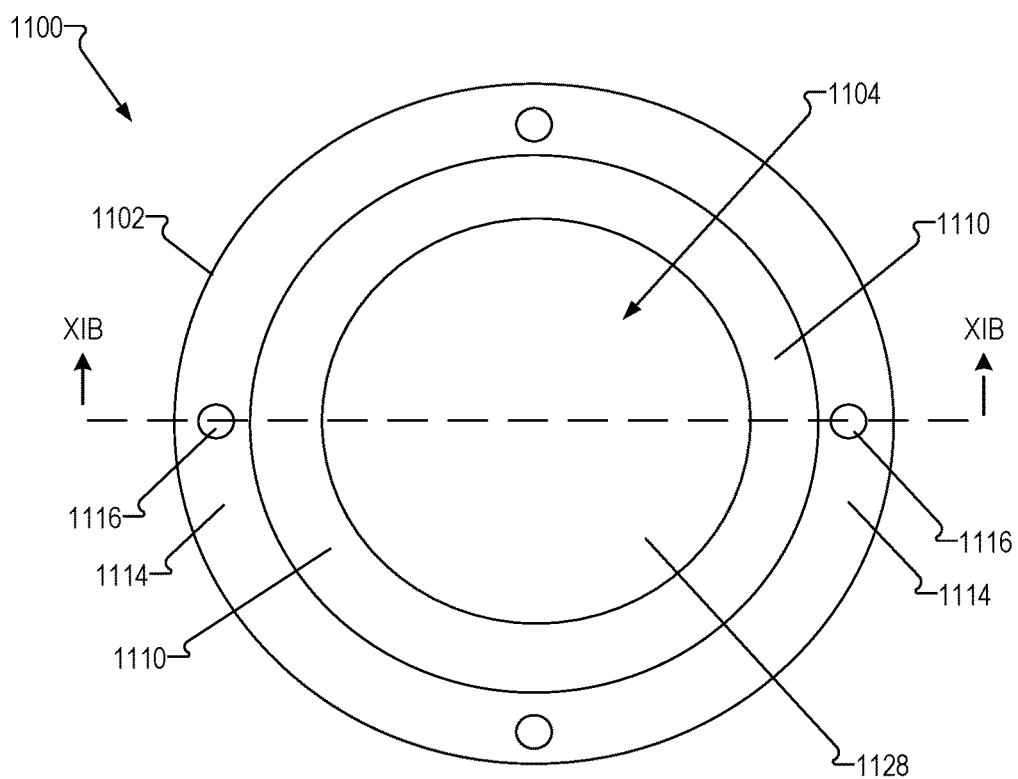
FIG. 11A shows a top view of an illustrative implementation of a fill port that may implement a fluid source included in the implantable drug delivery system of FIG. 1.
Figure 11B:
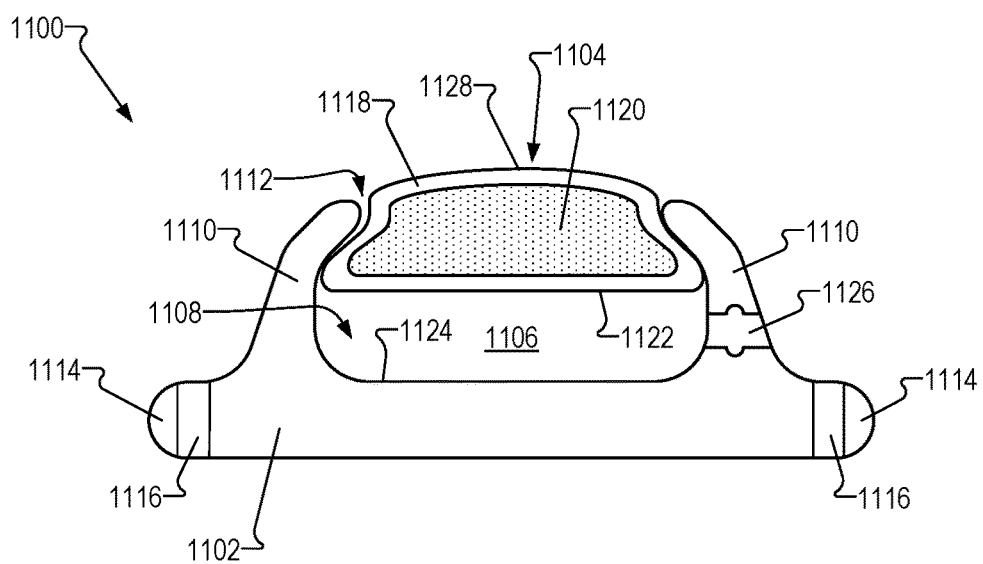
FIG. 11B shows a cross-sectional side view of the fill port of FIG. 11A.

In some examples, fluid source 108 may be implemented by a fill port. FIGS. 11A and 11B show an illustrative implementation of a fill port 1100 that may implement fluid source 108. FIG. 11A shows a top view of fill port 1100 and FIG. 11B shows a cross-sectional side view of fill port 1100 taken along the dashed line labeled XIB-XIB.

As shown in FIGS. 11A and 11B, fill port 1100 includes a main body 1102, a septum 1104, and a chamber 1106. Main body 1102 is formed of a rigid material, such as a hard plastic (e.g., PEEK) or a metal. Main body 1102 includes a cavity 1108 formed therein defined by side walls 1110 and an opening 1112 in an upper surface of main body 1102. Opening 1112 provides access to cavity 1108. As shown in FIG. 11B, inner surfaces of side walls 1110 are sloped or curved inward so that a size of opening 1112 is smaller than the size of cavity 1108. Alternatively, side walls 1110 may have any other suitable configuration (e.g., straight or sloped or curved outward) as may serve a particular implementation. Main body 1102 may be atraumatic, such as by having rounded edges and smooth curves. Main body 1102 may further include anchor portion 1114 with holes 1116 for attaching main body 1102 to the body, such as by bone screws, sutures, and/or staples. Main body 1102, cavity 1108, and opening 1112 may each have any suitable shape and size. For example, FIG. 11A shows that main body 1102, cavity 1108, and opening 1112 have a generally circular or rounded shape, as seen from a top view. In some examples, an outer diameter of main body 1102 is between about 18 mm and about 25 mm. In some examples, a diameter of cavity 1108 may be between about 5 mm and about 20 mm. In some examples, a thickness of main body 1102 may be between about 8 mm and about 10 mm.

Septum 1104 includes a sac 1118 and a soft gel 1120 in sac 1118. Sac 1118 may be formed, for example, of a soft elastomer (e.g., silicone), and gel 1120 may be any suitable soft gel (e.g., silicone gel). Septum 1104 is positioned in opening 1112 to seal off opening 1112. Septum 1104 may be attached to side walls 1110 with an adhesive. A bottom surface 1122 of septum 1104, side walls 1110 of cavity 1108, and a bottom surface 1124 of cavity 1108 define inner walls of chamber 1106. Chamber 1106 is a fluid chamber for receiving and/or holding a fluid (e.g., a neurotherapeutic drug) to be delivered to the target location by way of source catheter 104 and microcatheter 102.

Main body 1102 includes an opening 1126 in a side wall 1110 to fluidically connect source catheter 104 with chamber 1106. Source catheter 104 may be fluidically connected with chamber 1106 by way of a connector, as shown in FIG. 12.

Figure 12:
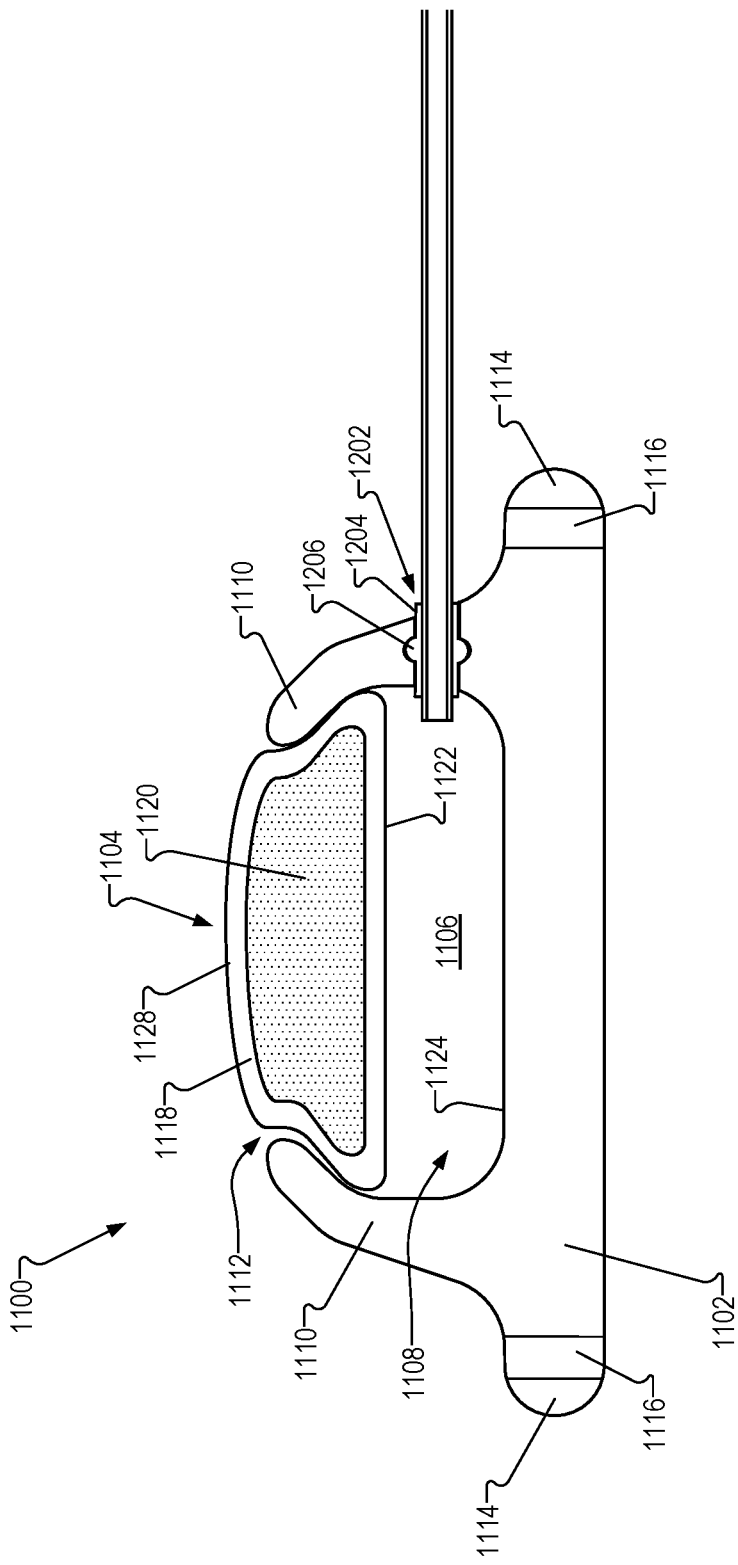
FIG. 12 shows a cross-sectional side view of the fill port of FIGS. 11A and 11B in an assembled state connected to a source catheter.

FIG. 12 is similar to FIG. 11B except that source catheter 104 is connected to fill port 1100 by way of a connector 1202. Connector 1202 may have any suitable configuration. As shown in FIG. 12, connector 1202 includes an elastomer sleeve 1204 positioned over the proximal end portion of source catheter 104. Sleeve 1204 may be formed to have a tight, friction-fit over source catheter 104 and a tight, friction-fit within opening 1126. For example, sleeve 1204 may have an inner diameter that is slightly smaller than the outer diameter of source catheter 104, and an outer diameter that is slightly larger than the inner diameter of opening 1126. An outer surface of sleeve 1204 may also include a protruding seal 1206 around the circumference of sleeve 1204. Seal 1206 is configured to engage with a correspondingly shaped channel in opening 1126 to secure sleeve 1204 in opening 1126 and prevent sleeve 1204 and source catheter 104 from disconnecting from fill port 1100. In alternative examples, connector 1202 may be implemented by a connector similar to connector 704-2 used for connecting source catheter 104 to cranial port 600. In some examples, connector 1202 and the correspondingly shaped opening 1126 may also be used in cranial port 600 in place of connector 704-1 and/or connector 704-2 and opening 614-1 and/or 614-2.

Chamber 1106 may be filled with a fluid (e.g., a neurotherapeutic drug) by inserting a non-coring needle through an upper surface 1128 of septum 1104 and into chamber 1106. As the fluid is pushed into chamber 1106 under pressure, the pressure pushes the fluid through source catheter 104, through connection assembly 106 (e.g., manifold 604 of cranial port 600), and through microcatheter 102 from which the fluid elutes to the target location. After the non-coring needle is removed from fill port 1100, gel 1120 resumes its crosslinked orientation, allowing septum 1104 to heal from the puncture.

The fluid may be pushed through system 100 in any suitable way. For example, in some implementations the fluid may be pushed through system 100 by a syringe connected to the non-coring needle.

Figure 13:
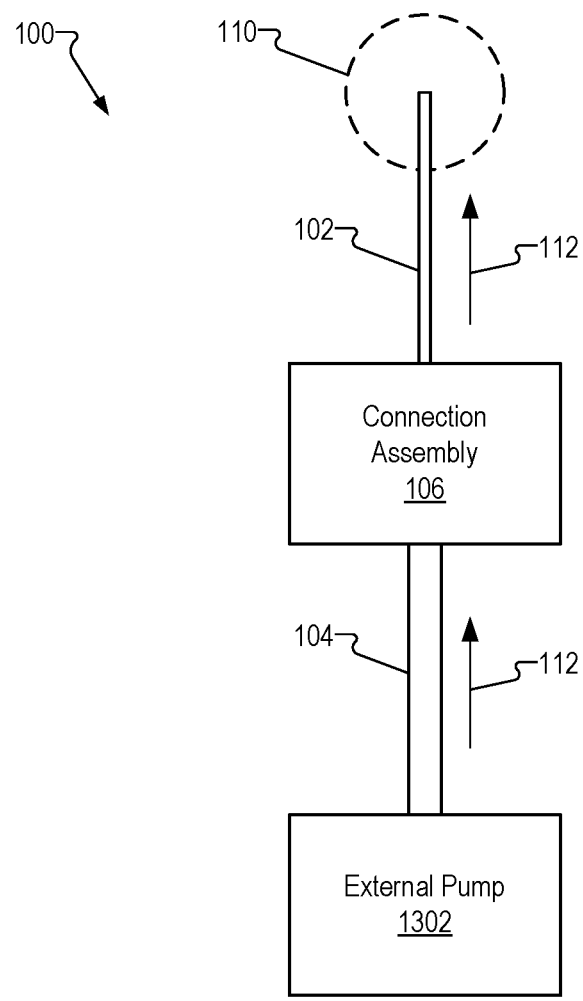
FIG. 13 shows a functional diagram of another illustrative implantable drug delivery system including an external pump.

FIG. 13 shows another implementation for pushing fluid through system 100 using an external pump 1302. FIG. 13 is similar to FIG. 1 except that, in FIG. 13, external pump 1302 (e.g., external to the recipient) is connected to source catheter 104 to push fluid through system 100. External pump 1302 may be connected to source catheter 104 in any suitable way, such as through a percutaneous access port or a cannula. External pump 1302 may be fluidically connected to an external fluid source (not shown) to provide fluid from the fluid source to microcatheter 102 by way of source catheter 104 and connection assembly 106.

Figure 14:
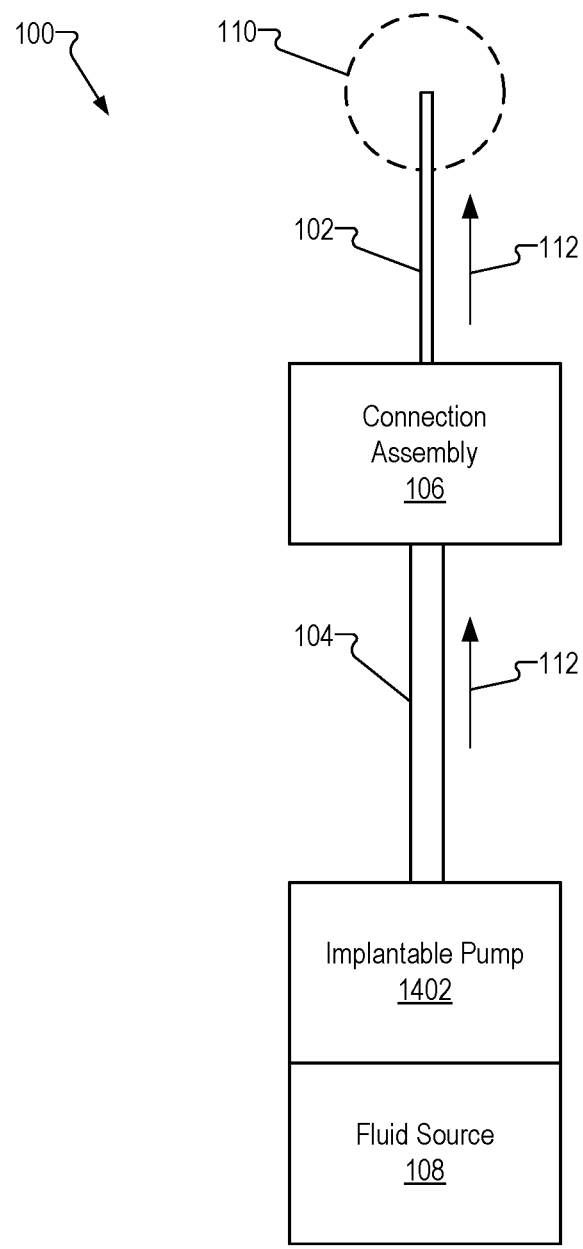
FIG. 14 shows a functional diagram of another illustrative implantable drug delivery system including an implantable pump.

FIG. 14 shows yet another implementation for pushing fluid through system 100 using an implantable pump 1402. FIG. 14 is similar to FIG. 1 except that, in FIG. 14, implantable pump 1402 is implanted in the recipient and connected between source catheter 104 and fluid source 108 (e.g., chamber 1106 of fill port 1100) to push fluid through system 100. Alternatively, implantable pump 1402 may be fluidically connected to source catheter 104 with fluid source 108 located in between source catheter 104 and implantable pump 1402. In yet further embodiments, implantable pump 1402 and fluid source 108 may be integrated as a single device. Fluid source 108 may be implantable in the recipient or may be external to the recipient.

In the implementations of FIGS. 13 and 14, source catheter 104 may be fluidically connected to external pump 1302 or implantable pump 1402 in any suitable way, including in any way described herein. In some examples, a proximal end portion of source catheter 104 is configured to connect to implantable pump 1402. Pumps 1302 and 1402 may be implemented by any suitable pump, such as a low-pressure pump or a peristaltic pump.

In embodiments in which an external device (e.g., a syringe and non-coring needle, external pump 1302, etc.) is used to push fluid through system 100, fluid source 108 may include an alignment unit configured to facilitate proper alignment of the external device with upper surface 1128 of septum 1104. In some examples, the alignment unit includes a metal object (e.g., a rod, a bead, a plate, a screw, etc.) that may be detected by the external device (e.g., by a metal detector, a magnetometer, etc.). The metal object may be included in (e.g., embedded in, attached to, etc.) fluid source 108 (e.g., in or on main body 1102). In some examples, the metal object includes bone screws or staples used to secure fluid source 108 to the body through holes 1116. In further examples, one or more components of fluid source 108 may be formed of metal (e.g., main body 1102).

Figure 15A:
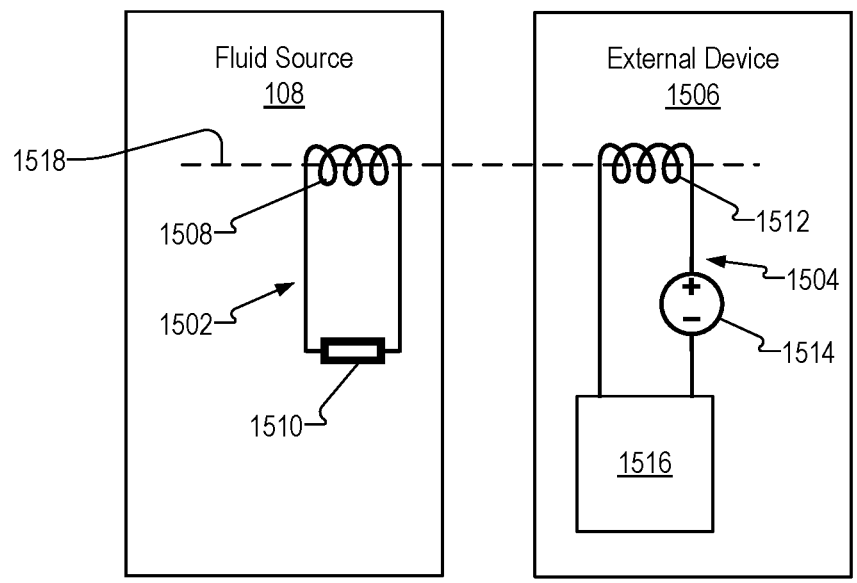
FIG. 15A shows a functional diagram of an illustrative implementation of an internal alignment circuit that may be included in a fluid source and an external alignment circuit that may be included in an external device.

In other examples, the alignment unit includes an internal alignment circuit in fluid source 108 that inductively couples to an external alignment circuit included in an external device (e.g., an external pump, a syringe, an alignment device, etc.). For example, FIG. 15A shows a functional diagram of an illustrative implementation of an internal alignment circuit 1502 in fluid source 108 and an external alignment circuit 1504 in an external device 1506. As shown, internal alignment circuit 1502 includes a conductive coil 1508 electrically connected with a load 1510 (e.g., a resistor). Internal alignment circuit 1502 may include any additional or alternative components as may serve a particular implementation (e.g., capacitors). External alignment circuit 1504 includes a conductive coil 1512 electrically connected to a current source 1514 and a measurement circuit 1516. External alignment circuit 1504 may include any additional or alternative components as may serve a particular implementation.

Current source 1514 is configured to generate a current through conductive coil 1512, and the current is inductively coupled onto conductive coil 1508 when external device 1506 is positioned near fluid source 108. The inductively coupled energy is then dissipated in load 1510. Measurement circuit 1516 is configured to measure the current drain or power transfer caused by internal alignment circuit 1502. Measurement circuit 1516 may have any suitable configuration. The measured current drain or power transfer increases as conductive coil 1512 is brought into alignment with axis 1518 of conductive coil 1508. A maximum current drain or power transfer occurs when conductive coil 1512 is aligned along the same axis 1518 of conductive coil 1508. Thus, external device 1506 can be brought into proper positional alignment with fluid source 108 based on the current drain measured by measurement circuit 1516 in external device 1506. That is, external device 1506 senses alignment by identifying a physical location where there is a maximum power transfer.

Figure 15B:
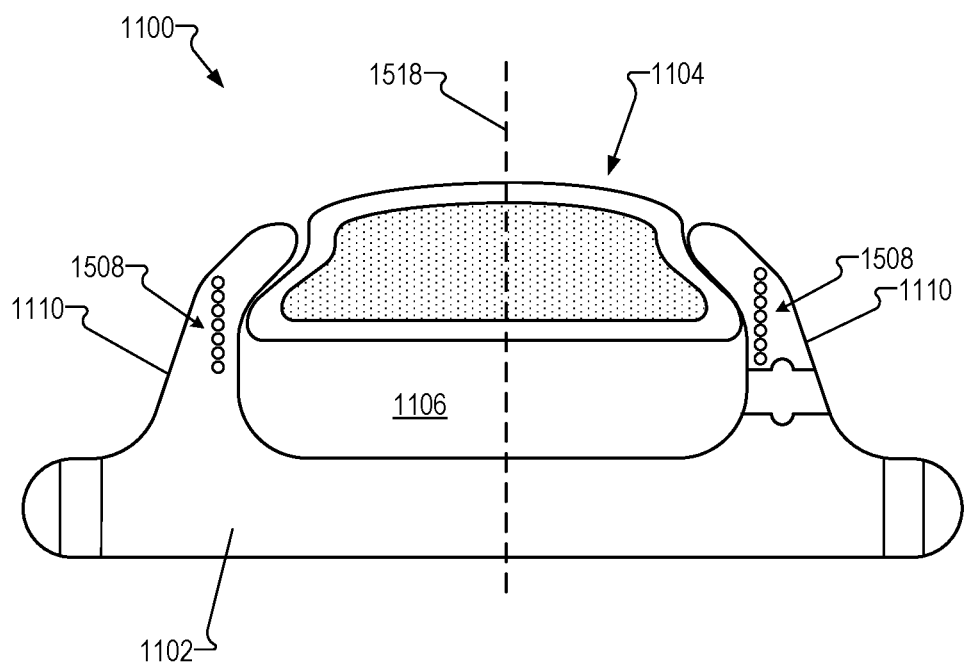
FIG. 15B shows an illustrative implementation of the fill port of FIGS. 11A-12 including the internal alignment circuit and in which an internal conductive coil is positioned around the chamber of the fill port.

Conductive coil 1508 of internal alignment circuit 1502 may be located in any suitable location within fluid source 108. For example, FIG. 15B shows an illustrative implementation of internal alignment circuit 1502 in fill port 1100. As shown, conductive coil 1508 is positioned within side walls 1110 around chamber 1106. Axis 1518 of conductive coil 1508 may be positioned at any suitable location, such as at the center of chamber 1106. However, conductive coil 1508 may be positioned at any suitable location within side walls 1110 and/or main body 1102. With the configuration shown in FIG. 15B, an external device (e.g., a needle and/or pump) may be properly aligned with fill port 1100 so that the needle penetrates septum 1104 and pushes fluid into chamber 1106 and through system 100.

Figure 16:
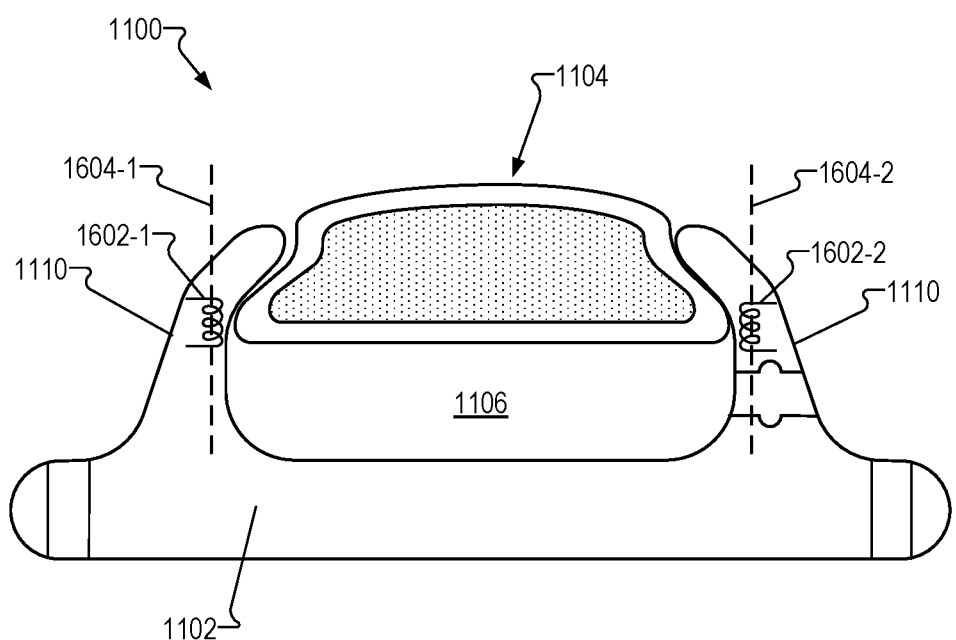
FIG. 16 shows another illustrative implementation of the fill port of FIGS. 11A-12 including the internal alignment circuit of FIG. 15A and in which a plurality of internal conductive coils are positioned within side walls of the fill port.

While FIG. 15B shows one conductive coil 1508, fill port 1100 may include any other number of conductive coils and internal alignment circuits 1502 as may serve a particular implementation (e.g., one or three or more). For example, FIG. 16 shows another illustrative implementation of internal alignment circuit 1502 in fill port 1100. As shown in FIG. 16, a first internal conductive coil 1602-1 and a second internal conductive coil 1602-2 are positioned within side walls 1110. Axes 1604-1 and 1604-2 of conductive coils 1602-1 and 1602-2 may be positioned with any suitable orientation. While FIG. 16 shows two conductive coils 1602, fill port 1100 may include any other number of conductive coils and internal alignment circuits as may serve a particular implementation (e.g., one or three or more). Conductive coils 1602-1 and 1602-2 may be connected to the same load or to different loads.

With the systems, assemblies, and methods described herein, various disorders and conditions may be treated more efficiently and with fewer side effects to the recipient. For example, system 100 may be used for the treatment of cancer (e.g., glioblastoma, tumors, etc.), Parkinson's disease, epilepsy (e.g., status epilepticus), Alzheimer's disease, Huntington's disease, multiple sclerosis, and psychiatric applications (e.g., depression, anxiety, etc.). System 100 may also be used for the treatment of other non-brain diseases or conditions (e.g., cancer). By delivering drugs directly to the target location instead of by intravenous administration, system 100 may avoid various system side effects and complications with conventional treatment methods.

In the examples described herein, various components and tools used to implement system 100 may be provided as a kit. For example, a kit may include any one or more of microcatheter 102, sleeve 210, an adhesive and applicator for attaching sleeve 210 to microcatheter 102, a stylet for implanting the distal end portion of microcatheter 102, a measuring tool (e.g., a ruler for measuring a proper length of microcatheter 102, and a knife or scissors for cutting microcatheter 102. Additionally, a kit may include any one or more of cranial port 600 or coupling 1000, connectors 704 (e.g., outer member 802, sealing member 804, pressing member 806, and/or a sleeve stopper), an adhesive and/or a sealer (e.g., an O-ring), fasteners (e.g., bone screws and screwdriver), a hex key or other tool (e.g., lever) for tightening pressing member 806 (retainer screw), and cover 904 for cranial port 600. Additionally, a kit may include any one or more of source catheter 104, a tunneling tool (for implanting source catheter 104), fluid source 108 (e.g., fill port 1100), connector 1202 (e.g., sleeve 1204), a needle (e.g., a non-coring needle), a syringe, a pump (e.g., external pump 1302, implantable pump 1402), external device 1506, and a knife or scissors for cutting source catheter 104. Additionally, a kit may include a sterilization kit for sterilizing an implant site and/or a fluid injection site on the body.

Various modifications may be made to system 100 and/or any of its components. For example, FIGS. 17A and 17B show another illustrative implementation of microcatheter 102. As shown, microcatheter 102 is implemented by a dual lumen catheter 1700. FIG. 17A shows a side view of dual lumen catheter 1700 and FIG. 17B shows a cross-sectional view of dual lumen catheter taken along the dashed line labeled XVIIB-XVIIB. As shown, dual lumen catheter 1700 includes a stylet lumen 1702 and a fluid delivery lumen 1704 side-by-side. A proximal end of stylet lumen 1702 is open while a distal end of stylet lumen 1702 is closed so that a stylet may be inserted into stylet lumen 1702 and used to implant a distal end of dual lumen catheter at a target location. A proximal end portion of fluid delivery lumen 1704 is configured to be fluidically connected to the distal end portion of source catheter 104, such as in any of the ways described herein. Accordingly, as shown in FIG. 17A the proximal end portion of fluid delivery lumen 1704 is longer than the proximal end portion of stylet lumen 1702. The distal end portion of fluid delivery lumen 1704 is configured to be implanted at the target location and elute a fluid to the target location through an elution opening (not shown). The elution opening may be configured in any way described herein.

In another modification, fluid source 108 may be included in cranial port 600 so that source catheter 104 is not needed. For example, manifold 604 may implement a fill port (e.g., chamber 612 of manifold 604 may implement chamber 1106 of fill port 1100). Accordingly, cranial port 600 may include a septum to allow chamber 612 to be filled with fluid by an external device.

As mentioned above, sleeve 210 may be used in system 100 as a one-way valve to prevent fluid from flowing back into microcatheter 102 through elution opening 204. It will be recognized that this one-way sleeve valve may be used in applications other than for a microcatheter and/or for systems other than system 100. For example, sleeve 210 may be used as a one-way valve for any other catheter (e.g., a central venous catheter). Additionally, sleeve 210 may be used in other medical and non-medical applications.

The systems, assemblies, and methods described herein offer numerous benefits and advantages over conventional systems, assemblies, and methods. For example, with the systems, assemblies, and methods described herein neurotherapeutic drugs may be delivered directly to a target location within the recipient with minimal systemic side effects. Additionally, the distal end portion of the microcatheter may be positioned at or near the target location, thereby increasing the efficiency of drug delivery.

Furthermore, the microcatheter and the source catheter may each be configured to suit the different functions that each catheter serves without sacrificing performance of the catheters or the system as a whole. For example, the microcatheter may be small, soft, and flexible so that it can be implanted in or near delicate tissue, such as brain tissue, without injuring the tissue. The microcatheter may also be implanted at the target location under stereotactic guidance and/or image guidance (e.g., radioscopic or fluorescence guidance). On the other hand, the source catheter may be more physically and mechanically robust to prevent kinking or collapsing and to allow more physically demanding implantation techniques, such as tunneling and pulling. Thus, the fluid source may be implanted at a location far away from the target location. For example, the target location may be the brain while the fluid source may be implanted at the thorax, which has more space than the head and less hair that carries pathogens. In this way, the fluid source does not protrude from the head and is less susceptible to receiving pathogens that are commonly carried in hair. Moreover, this configuration may be more comfortable and cosmetically appealing to the recipient.

Furthermore, the systems, assemblies, and methods described herein may permit more frequent or even on-demand delivery of drug to the target location. For example, a drug may be administered to the target location as needed, such as at the onset of a seizure. A drug may also be delivered to the target location with more frequency and with greater ease. For example, the drug may be delivered to the target location (e.g., the brain) with a simple injection through the recipient's skin into the fluid source. Moreover, the drug may be replenished or even changed as needed without surgical intervention.

Advantages and features of the present disclosure can be further described by the following statements.

1. A drug delivery system implantable in a recipient, comprising: a connection assembly; a source catheter comprising: a proximal end portion configured to be fluidically connected to a fluid source configured to provide a fluid; and a distal end portion configured to be fluidically connected to the connection assembly; and a microcatheter comprising: a proximal end portion configured to be fluidically connected to the connection assembly; and a distal end portion comprising an elution opening configured to elute the fluid to a target location within the recipient.

2. The drug delivery system of statement 1, wherein the target location comprises a brain of the recipient.

3. The drug delivery system of statement 2, wherein the distal end portion of the microcatheter is implantable in parenchymal tissue of the brain.

4. The drug delivery system of statement 2 or 3, wherein the fluid comprises a neurotherapeutic drug.

5. The drug delivery system of any of statements 2-4, wherein the connection assembly comprises a cranial port comprising: a base member configured to be attached to a skull of the recipient; and a manifold on the base member; wherein the proximal end portion of the microcatheter is configured to be fluidically connected to the distal end portion of the source catheter by way of the manifold.

6. The drug delivery system of statement 5, wherein the manifold is integrally formed with the base member.

7. The drug delivery system of statement 5 or 6, wherein the base member comprises an access hole for accessing a burr hole in the skull, the burr hole providing access to the brain.

8. The drug delivery system of statement 7, wherein: the base member further comprises a guide channel extending from the access hole to an outside edge of the base member; and the guide channel is configured to secure the microcatheter when the distal end portion of the microcatheter is implanted in the brain.

9. The drug delivery system of any of statements 5-8, further comprising a first connector for connecting the microcatheter to the manifold, the first connector comprising: a hollow first outer member having a first inner portion, a proximal end wall, and an opening in the proximal end wall; a first sealing member having a first inner channel configured to receive the proximal end portion of the microcatheter, the first sealing member being configured to be positioned in the first inner portion of the first outer member; and a first pressing member configured to press the first sealing member to compress the first sealing member around the proximal end portion of the microcatheter when the proximal end portion of the microcatheter is positioned through the first inner channel of the first sealing member.

10. The drug delivery system of statement 9, wherein the first sealing member is configured to seal the first inner portion of the first outer member when pressed by the first pressing member.

11. The drug delivery system of statement 9 or 10, wherein an inner diameter of the first inner channel of the first sealing member is about equal to or less than an outer diameter of the microcatheter.

12. The drug delivery system of any of statements 9-11, wherein: the first inner portion of the first outer member comprises a distal inner portion and a proximal inner portion; the first sealing member is configured to be positioned in the proximal inner portion of the first outer member; and the first pressing member is configured to be positioned in the distal inner portion of the first outer member.

13. The drug delivery system of statement 12, wherein: the distal inner portion of the first outer member is threaded; and the first pressing member comprises a retainer screw.

14. The drug delivery system of any of statements 9-13, further comprising a second connector for connecting the source catheter to the manifold, the second connector comprising: a hollow second outer member having a second inner portion, a distal end wall, and an opening in the distal end wall; a second sealing member having a second inner channel configured to receive the distal end portion of the source catheter, the second sealing member being configured to be positioned in the second inner portion of the second outer member; and a second pressing member configured to press the second sealing member to compress the second sealing member around the distal end portion of the source catheter when the distal end portion of the source catheter is positioned through the second inner channel of the second sealing member.

15. The drug delivery system of any of statements 9-14, wherein: the manifold comprises a first opening for connecting the microcatheter and a second opening for connecting the source catheter; and the first outer member is secured in the first opening.

16. The drug delivery system of any of the preceding statements, wherein a hardness of the microcatheter is less than a hardness of the source catheter.

17. The drug delivery system of any of the preceding statements, wherein a hardness of the microcatheter is between about 20 Shore A durometer and about 50 Shore A durometer.

18. The drug delivery system of any of the preceding statements, wherein the source catheter comprises an inner braid.

19. The drug delivery system of any of the preceding statements, wherein at least one of: an inner diameter of the microcatheter is smaller than an inner diameter of the source catheter; or an outer diameter of the microcatheter is smaller than an outer diameter of the source catheter.

20. The drug delivery system of statement 19, wherein the outer diameter of the microcatheter is between about 0.5 mm and about 1.0 mm.

21. The drug delivery system of statement 19 or 20, wherein the outer diameter of the source catheter is between about 1.0 mm and about 1.5 mm.

22. The drug delivery system of any of statements 19-21, wherein the inner diameter of the microcatheter is between about 0.30 mm and about 0.80 mm.

23. The drug delivery system of any of statements 19-22, wherein the inner diameter of the source catheter is between about 0.5 mm and about 1.0 mm.

24. The drug delivery system of any of the preceding statements, wherein a wall thickness of the microcatheter is between about 0.05 mm and about 0.15 mm.

25. The drug delivery system of any of the preceding statements, wherein a diameter of the elution opening is between about 0.25 mm and about 0.5 mm.

26. The drug delivery system of any of the preceding statements, wherein the microcatheter is configured to be implanted in the recipient under at least one of image guidance or stereotactic guidance.

27. The drug delivery system of any of the preceding statements, wherein the microcatheter further comprises one or more imaging markers.

28. The drug delivery system of any of the preceding statements, wherein the microcatheter is configured to be implanted in the recipient with a stylet.

29. The drug delivery system of any of the preceding statements, wherein: a distal tip of the microcatheter is sealed; the elution opening is in a side wall of the distal end portion of the microcatheter; and the microcatheter further comprises a one-way valve at the elution opening.

30. The drug delivery system of statement 29, wherein the one-way valve comprises a flexible sleeve on the microcatheter and covering the elution opening.

31. The drug delivery system of statement 30, wherein a distal end portion of the sleeve or a proximal end portion of the sleeve is adhered to the side wall of the distal end portion of the microcatheter.

32. The drug delivery system of statement 30 or 31, wherein: the sleeve has a closed distal tip; and the distal tip of the microcatheter is sealed by the closed distal tip of the sleeve.

33. The drug delivery system of any of the preceding statements, wherein the connection assembly comprises a coupling.

34. The drug delivery system of any of the preceding statements, wherein the fluid source comprises: a body member comprising a cavity and an opening, in a surface of the body member, to the cavity; a septum positioned in the opening and comprising a gel in a sac; and a chamber defined by the cavity of the body member and the septum.

35. The drug delivery system of any of the preceding statements, further comprising an implantable pump configured to push the fluid from the fluid source to the target location by way of the source catheter and the microcatheter.

36. The drug delivery system of any of the preceding statements, further comprising an external device configured to push the fluid from the fluid source to the target location by way of the source catheter and the microcatheter.

37. The drug delivery system of statement 36, wherein the external device comprises a syringe or an external pump.

38. The drug delivery system of statement 36 or 37, wherein the fluid source comprises an alignment unit configured to facilitate alignment of the external device with the fluid source.

39. The drug delivery system of statement 38, wherein the alignment unit comprises one or more metal objects configured to be detected by a metal detector on the external device.

40. The drug delivery system of statement 38 or 39, wherein: the alignment unit comprises an alignment circuit including a first conductive coil electrically connected to a load; and the first conductive coil is configured to inductively couple with a second conductive coil included in the external device when the external device is aligned with the fluid source.

41. A method comprising: implanting a distal end portion of a microcatheter at a target location within a recipient, the distal end portion of the microcatheter comprising an elution opening for eluting a fluid to the target location; fluidically connecting a proximal end portion of the microcatheter to a distal end portion of a source catheter by way of a connection assembly; and fluidically connecting a proximal end portion of the source catheter to a fluid source configured to provide the fluid to the microcatheter.

42. The method of statement 41, wherein the target location comprises a brain of the recipient.

43. The method of statement 42, wherein the target location comprises parenchymal tissue of the brain.

44. The method of statement 42 or 43, wherein the fluid comprises a neurotherapeutic drug.

45. The method of any of statements 42-44, wherein the implanting the distal end portion of the microcatheter comprises: forming a burr hole in a skull of the recipient; and inserting the distal end portion of the microcatheter through the burr hole.

46. The method of statement 45, wherein: the connection assembly comprises a cranial port comprising: a base member; and a manifold on the base member; the method further comprises attaching the cranial port to the skull; and the fluidically connecting the proximal end portion of the microcatheter to the distal end portion of the source catheter by way of the connection assembly comprises: connecting the proximal end portion of the microcatheter to the manifold; and connecting the distal end portion of the source catheter to the manifold.

47. The method of statement 46, wherein: the base member comprises an access hole for accessing the burr hole and a guide channel extending from the access hole to an outside edge of the base member; and the method further comprises positioning the microcatheter in the guide channel.

48. The method of statement 46 or 47, wherein the connecting the proximal end portion of the microcatheter to the manifold comprises: positioning a first sealing member in a first inner portion of a hollow first outer member, the first outer member having a proximal end wall and an opening in the proximal end wall; inserting the proximal end portion of the microcatheter through a first inner channel of the first sealing member and through the opening in the proximal end wall; and causing a first pressing member to press the first sealing member to compress the first sealing member around the proximal end portion of the microcatheter.

49. The method of statement 48, wherein: the first inner portion of the first outer member comprises a distal inner portion and a proximal inner portion; the first sealing member is positioned in the proximal inner portion of the first outer member; and the causing the first pressing member to press the first sealing member comprises positioning the first pressing member in the distal inner portion of the first outer member.

50. The method of statement 49, wherein: the distal inner portion of the first outer member is threaded; the first pressing member comprises a retainer screw; and the causing the first pressing member to press the first sealing member further comprises tightening the retainer screw.

51. The method of any of statements 48-50, wherein the connecting the distal end portion of the source catheter to the manifold comprises: positioning a second sealing member in a second inner portion of a hollow second outer member, the second outer member having a distal end wall and an opening in the distal end wall; inserting the distal end portion of the source catheter through a second inner channel of the second sealing member and through the opening in the distal end wall; and causing a pressing member to press the second sealing member to compress the second sealing member around the distal end portion of the source catheter.

52. The method of any of statements 41-51, wherein the implanting the distal end portion of the microcatheter comprises: inserting a stylet in the distal end portion of the microcatheter; using the stylet to position the distal end portion of the microcatheter at the target location; and removing the stylet from the microcatheter after the distal end portion of the microcatheter is positioned at the target location.

53. The method of any of statements 41-52, wherein the microcatheter is implanted in the recipient under at least one of image guidance or stereotactic guidance.

54. The method of statement 53, wherein the microcatheter comprises one or more imaging markers.

55. The method of any of statements 41-54, further comprising: implanting the fluid source in the recipient; and implanting the source catheter in the recipient.

56. The method of statement 55, wherein the implanting the source catheter comprises tunneling the source catheter through the recipient from the fluid source to the proximal end portion of the microcatheter.

57. The method of statement 55 or 56, wherein the fluid source is implanted in a thorax of the recipient.

58. The method of any of statements 41-57, further comprising: providing the fluid to the fluid source; and pushing the fluid from the fluid source to the target location by way of the source catheter and the microcatheter.

59. The method of statement 58, further comprising implanting an implantable pump; wherein the pushing the fluid from the fluid source to the target location is performed by the implantable pump.

60. The method of statement 58 or 59, further comprising aligning, by way of an alignment unit included in the fluid source, an external device with the fluid source; wherein at least one of the providing the fluid to the fluid source or the pushing the fluid from the fluid source to the target location is performed with the external device.

61. A connection assembly for an implantable drug delivery system, the connection assembly comprising: a base member configured to be attached to a skull of a recipient; and a manifold on the base member and configured to couple a proximal end portion of a microcatheter to a distal end portion of a source catheter.

62. The connection assembly of statement 61, wherein the manifold is integrally formed with the base member.

63. The connection assembly of statement 61 or 62, wherein the base member comprises an access hole for accessing a burr hole in the skull, the burr hole providing access to a brain of the recipient.

64. The connection assembly of statement 63, wherein: the base member further comprises a first guide channel extending from the access hole to an outside edge of the base member; and the first guide channel is configured to secure the microcatheter when a distal end portion of the microcatheter is implanted in the brain of the recipient.

65. The connection assembly of statement 64, wherein: the base member further comprises a second guide channel extending along the outside edge of the base member from the first guide channel to an opening to the manifold; and the second guide channel is configured to secure the microcatheter when the distal end portion of the microcatheter is implanted in the brain of the recipient.

66. The connection assembly of any of statements 61-65, further comprising a first connector for connecting the microcatheter to the manifold, the first connector comprising: a hollow first outer member having a first inner portion, a proximal end wall, and an opening in the proximal end wall; a first sealing member having a first inner channel configured to receive the proximal end portion of the microcatheter, the first sealing member being configured to be positioned in the first inner portion of the first outer member; and a first pressing member configured to press the first sealing member to compress the first sealing member around the proximal end portion of the microcatheter when the proximal end portion of the microcatheter is positioned through the first inner channel of the first sealing member.

67. The connection assembly of statement 66, wherein the first sealing member is configured to seal the first inner portion of the first outer member when pressed by the first pressing member.

68. The connection assembly of statement 66 or 67, wherein an inner diameter of the first inner channel of the first sealing member is about equal to or less than an outer diameter of the microcatheter.

69. The connection assembly of any of statements 66-68, wherein: the first inner portion of the first outer member comprises a distal inner portion and a proximal inner portion; the first sealing member is configured to be positioned in the proximal inner portion of the first outer member; and the first pressing member is configured to be positioned in the distal inner portion of the first outer member.

70. The connection assembly of statement 69, wherein: the distal inner portion of the first outer member is threaded; and the first pressing member comprises a retainer screw.

71. The connection assembly of any of statements 66-70, wherein: the manifold comprises a first opening for connecting the microcatheter; and the first outer member is secured in the first opening.

72. The connection assembly of any of statements 66-71, further comprising a second connector for connecting the source catheter to the manifold, the second connector comprising: a hollow second outer member having a second inner portion, a distal end wall, and an opening in the distal end wall; a second sealing member having a second inner channel configured to receive the distal end portion of the source catheter, the second sealing member being configured to be positioned in the second inner portion of the second outer member; and a second pressing member configured to press the second sealing member to compress the second sealing member around the distal end portion of the source catheter when the distal end portion of the source catheter is positioned through the second inner channel of the second sealing member.

73. The connection assembly of statement 72, wherein: the manifold comprises a second opening for connecting the source catheter; and the second outer member is secured in the second opening.

74. The connection assembly of any of statements 61-73, further comprising a cover configured to cover the base member and the manifold.

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A drug delivery system implantable in a recipient, comprising:
a connection assembly comprising a cranial port, the cranial port comprising;
a base member configured to be attached to a skull of the recipient and comprising an access hole for accessing a burr hole in the skull of the recipient; and
a manifold on the base member;
a source catheter comprising:

a proximal end portion configured to be fluidically connected to an implantable fluid source configured to provide a fluid; and a distal end portion configured to be fluidically connected to the connection assembly; and a microcatheter comprising:

a proximal end portion configured to be fluidically connected to the connection assembly; and a distal end portion comprising an elution opening configured to elute the fluid to a target location within the recipient;

wherein a hardness of the microcatheter is less than a hardness of the source catheter;

wherein the microcatheter is configured to be positioned through the access hole and along an outside edge of the base member; and wherein the proximal end portion of the microcatheter is configured to be fluidically connected to the distal end portion of the source catheter by way of the manifold.

2. The drug delivery system of claim 1, wherein at least one of:

an inner diameter of the microcatheter is smaller than an inner diameter of the source catheter; or an outer diameter of the microcatheter is smaller than an outer diameter of the source catheter.

3. The drug delivery system of claim 1, wherein:

a distal tip of the microcatheter is sealed;

the elution opening is in a side wall of the distal end portion of the microcatheter; and the microcatheter further comprises a one-way valve at the elution opening, the one-way valve comprising a flexible sleeve on the microcatheter and covering the elution opening.

4. The drug delivery system of claim 3, wherein a distal end portion of the sleeve or a proximal end portion of the sleeve is adhered to the side wall of the distal end portion of the microcatheter.

5. The drug delivery system of claim 3, wherein:

the sleeve has a closed distal tip; and the distal tip of the microcatheter is sealed by the closed distal tip of the sleeve.

6. The drug delivery system of claim 1, wherein the fluid source comprises:

a body member comprising a cavity and an opening, in a surface of the body member, to the cavity;

a septum positioned in the opening and comprising a gel in a sac; and a chamber defined by the cavity of the body member and the septum.

7. The drug delivery system of claim 1, further comprising an implantable pump configured to push the fluid from the fluid source to the target location by way of the source catheter and the microcatheter.

8. The drug delivery system of claim 1, wherein:

the fluid source comprises an alignment unit configured to facilitate alignment of an external device with the fluid source, the external device being configured to push the fluid from the fluid source to the target location by way of the source catheter and the microcatheter; and the alignment unit comprises at least one of:

a metal object configured to be detected by a metal detector included in the external device; or an alignment circuit including a first conductive coil electrically connected to a load, the first conductive coil configured to inductively couple with a second conductive coil included in the external device when the external device is aligned with the fluid source.

9. A method comprising:

attaching a cranial port to a skull of a recipient, the cranial port comprising:

a base member comprising an access hole for accessing a burr hole in the skull of the recipient; and a manifold on the base member;

implanting a distal end portion of a microcatheter at a target location within the recipient, the distal end portion of the microcatheter comprising an elution opening for eluting a fluid to the target location;

fluidically connecting a proximal end portion of the microcatheter to a distal end portion of a source catheter, the fluidically connecting comprising:

positioning the microcatheter through the access hole and along an outside edge of the base member;

connecting the proximal end portion of the microcatheter to the manifold; and connecting the distal end portion of the source catheter to the manifold; and fluidically connecting a proximal end portion of the source catheter to a fluid source configured to provide the fluid to the microcatheter;

wherein a hardness of the microcatheter is less than a hardness of the source catheter.

10. The method of claim 9, wherein:

the base member further comprises a guide channel extending from the access hole to the outside edge of the base member; and the microcatheter is positioned in the guide channel.

11. The method of claim 9, wherein connecting the proximal end portion of the microcatheter to the manifold comprises:

positioning a first sealing member in a first inner portion of a hollow first outer member, the first outer member having a proximal end wall and an opening in the proximal end wall;

inserting the proximal end portion of the microcatheter through a first inner channel of the first sealing member and through the opening in the proximal end wall; and causing a first pressing member to press the first sealing member to compress the first sealing member around the proximal end portion of the microcatheter.

12. The method of claim 11, wherein:

the first inner portion of the first outer member comprises a distal inner portion and a proximal inner portion;

the first sealing member is positioned in the proximal inner portion of the first outer member; and the causing the first pressing member to press the first sealing member comprises positioning the first pressing member in the distal inner portion of the first outer member.

13. The method of claim 11, wherein the connecting the distal end portion of the source catheter to the manifold comprises:

positioning a second sealing member in a second inner portion of a hollow second outer member, the second outer member having a distal end wall and an opening in the distal end wall;

inserting the distal end portion of the source catheter through a second inner channel of the second sealing member and through the opening in the distal end wall; and causing a pressing member to press the second sealing member to compress the second sealing member around the distal end portion of the source catheter.

14. A connection assembly for an implantable drug delivery system, the connection assembly comprising:

a base member configured to be attached to a skull of a recipient, the base member comprising:
   an access hole for accessing a burr hole in the skull of the recipient; and
   a first guide channel that extends from the access hole to an outside edge of the base member;
a manifold on the base member and configured to fluidically couple a proximal end portion of a microcatheter to a distal end portion of a source catheter;
wherein the base member is configured to position the microcatheter through the access hole, within the first guide channel, and along the outside edge of the base member when a distal end portion of the microcatheter is implanted in a brain of the recipient.

15. The connection assembly of claim 14, wherein the manifold is integrally formed with the base member.

16. The connection assembly of claim 14, wherein:
the base member further comprises a second guide channel extending along the outside edge of the base member from the first guide channel to an opening to the manifold; and
the base member is further configured to position the microcatheter within the second guide channel when the distal end portion of the microcatheter is implanted in the brain of the recipient.

17. The connection assembly of claim 14, further comprising a first connector for connecting the microcatheter to the manifold, the first connector comprising:
a hollow first outer member having a first inner portion, a proximal end wall, and an opening in the proximal end wall;
a first sealing member having a first inner channel configured to receive the proximal end portion of the microcatheter, the first sealing member being configured to be positioned in the first inner portion of the first outer member; and
a first pressing member configured to press the first sealing member to compress the first sealing member around the proximal end portion of the microcatheter when the proximal end portion of the microcatheter is positioned through the first inner channel of the first sealing member.

18. The connection assembly of claim 17, wherein the first sealing member is configured to seal the first inner portion of the first outer member when pressed by the first pressing member.

19. The connection assembly of claim 17, wherein an inner diameter of the first inner channel of the first sealing member is about equal to or less than an outer diameter of the microcatheter.

20. The connection assembly of claim 17, wherein:
the first inner portion of the first outer member comprises a distal inner portion and a proximal inner portion;
the first sealing member is configured to be positioned in the proximal inner portion of the first outer member; and
the first pressing member is configured to be positioned in the distal inner portion of the first outer member.

21. The connection assembly of claim 20, wherein:
the distal inner portion of the first outer member is threaded; and
the first pressing member comprises a retainer screw.

22. The connection assembly of claim 17, wherein:
the manifold comprises a first opening for connecting the microcatheter; and
the first outer member is secured in the first opening.

23. The connection assembly of claim 17, further comprising a second connector for connecting the source catheter to the manifold, the second connector comprising:
a hollow second outer member having a second inner portion, a distal end wall, and an opening in the distal end wall;
a second sealing member having a second inner channel configured to receive the distal end portion of the source catheter, the second sealing member being configured to be positioned in the second inner portion of the second outer member; and
a second pressing member configured to press the second sealing member to compress the second sealing member around the distal end portion of the source catheter when the distal end portion of the source catheter is positioned through the second inner channel of the second sealing member.

24. The connection assembly of claim 23, wherein:
the manifold comprises a second opening for connecting the source catheter; and
the second outer member is secured in the second opening.

25. The connection assembly of claim 14, further comprising a cover configured to cover the base member and the manifold.

* * * * *